(12) United States Patent
Urbina et al.

(10) Patent No.: US 11,542,487 B2
(45) Date of Patent: Jan. 3, 2023

(54) BETA-AMYLASE ENZYMES

(71) Applicant: BASF SE, Ludwigshafen am Rhein (DE)

(72) Inventors: Hugo Urbina, San Diego, CA (US); Tong Li, San Diego, CA (US); Jared Dennis, San Diego, CA (US); Xuqiu Tan, San Diego, CA (US); Adrienne Huston Davenport, San Diego, CA (US); Jochen Kutscher, Balzheim (DE); Kristine W. Chang, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 125 days.

(21) Appl. No.: 16/757,993

(22) PCT Filed: Oct. 17, 2018

(86) PCT No.: PCT/IB2018/001276
§ 371 (c)(1),
(2) Date: Apr. 21, 2020

(87) PCT Pub. No.: WO2019/081976
PCT Pub. Date: May 2, 2019

(65) Prior Publication Data
US 2020/0318089 A1    Oct. 8, 2020

Related U.S. Application Data

(60) Provisional application No. 62/576,930, filed on Oct. 25, 2017.

(51) Int. Cl.
*C12N 9/26*    (2006.01)

(52) U.S. Cl.
CPC .... *C12N 9/2425* (2013.01); *C12Y 302/01002* (2013.01)

(58) Field of Classification Search
None
See application file for complete search history.

(56) References Cited

FOREIGN PATENT DOCUMENTS

EP    0337 090    * 10/1989    ............. C12N 15/00

OTHER PUBLICATIONS

Kitamoto et al.,"Cloning and Sequencing of the Gene encoding Thermophilic beta-amylase of Clostridium thermosulfurogenes", Journal of Bateriology, vol. 170, No. 12, pp. 5848-5854 Dec. 1988 (Year: 1988).*

* cited by examiner

*Primary Examiner* — Anand U Desai
(74) *Attorney, Agent, or Firm* — DLA Piper LLP (US)

(57) ABSTRACT

Variant polypeptides having beta-amylase activity and methods of making and using the enzymes in baking, detergents, personal care products, in the processing of textiles, in pulp and paper processing, in the production of ethanol, lignocellulosic ethanol, or syrups; as viscosity breakers in oilfield and mining industries.

7 Claims, 2 Drawing Sheets
Specification includes a Sequence Listing.

SEQUENCE LISTING

```
<160> NUMBER OF SEQ ID NOS: 7

<210> SEQ ID NO 1
<211> LENGTH: 1560
<212> TYPE: DNA
<213> ORGANISM: Artificial Sequence
<220> FEATURE:
<223> OTHER INFORMATION: Synthetic generation

<400> SEQUENCE: 1
tccatcgctc caaacttcaa agttttcgtc atgggaccac tggagaaggt cactgatttc      60
aacgccttca aggaccagtt gatcacccct aaaaataacg gtgtctacgg gattaccact     120
gatatttggt ggggttacgt tgagaacgcc ggagagaacc aattcgactg gtcttattat     180
aagacttatg ctgacaccgt cagagctgct ggattgaagt gggtcccaat catgtcaacc     240
catgcttgtg gtggaaacgt tggtgacact gttaacattc aataccctc ttgggtgtgg     300
```

```
accaaagaca cccaagacaa tatgcaatat aaggacgagg ctggtaactg ggataatgag    360
gctgtctctc catggtactc cggcttgaca cagctgtaca acgagttcta ctcttccttc    420
gctagcaact tttcttccta caaagatatt atcactaaga tctacatctc tggtggtcca    480
tctggtgagt tgcgctaccc ttcctataac ccatcccacg gttggactta ccctggtaga    540
ggttctttgc agtgttattc taaggctgca atcacctctt tccagaacgc tatgaagagc    600
aagtacggaa ctattgccgc agtcaattct gcttggggaa cctccctaac tgacttctct    660
cagatttctc ctccaaccga tggtgacaat ttctttacta atggttacaa gacaacttac    720
ggtaacgatt tccttacctg gtaccaaagt gtcttgacta atgagttggc taacatcgct    780
tctgtcgctc attcctgctt cgatccagtc ttcaatgtgc ctattggtgc aagattgcc     840 ggtgtacact ggctttataa ctcccccaact atgcctcacg cagccgagta ctgtgccggt    900
tactataatt actcgacttt gctagaccag tttaaggcca gtaacttggc tatgactttc    960
acctgtctcg aaatggatga ctcaaacgcc tacgtttctc catattactc tgctccaatg   1020
accttagttc actacgttgc caatttggct aacaataagg gcattgttca aatggtgag    1080 aacgccttgg ctatcagcaa caataaccaa gcttatgtta actgtgctaa tgagctcacc   1140
ggttacaact tctctggctt cactttgttg cgtttgagta acattgtcaa ctcagacggc   1200
tctgtcacct ccgagatggc tccattcgtt atcaacattg ttactttgac tccaaacggt   1260
accattcctg ttactttcac catcaacaac gctactacct actacggcca aaacgtttat   1320
attgttggta gcacctctga cttgggtaat tggaatacga cttacgctag aggtcctgcc   1380
tcctgcccaa actatcctac ctggactatc actcttaatc ttcttccagg tgaacaaatt   1440
caattcaagg ctgtgaagat tgactcttct ggtaacgtta cttgggaagg tggttcaaac   1500
cacacttaca ctgtgccgac ttccggaact ggttctgtga ctattacctg gcaaaactaa   1560
```

```
<210> SEQ ID NO 2
<211> LENGTH: 519
<212> TYPE: PRT
<213> ORGANISM: Clostridium thermosulfurogenes

<400> SEQUENCE: 2

Ser Ile Ala Pro Asn Phe Lys Val Phe Val Met Gly Pro Leu Glu Lys
1               5                   10                  15

Val Thr Asp Phe Asn Ala Phe Lys Asp Gln Leu Ile Thr Leu Lys Asn
            20                  25                  30

Asn Gly Val Tyr Gly Ile Thr Thr Asp Ile Trp Trp Gly Tyr Val Glu
        35                  40                  45

Asn Ala Gly Glu Asn Gln Phe Asp Trp Ser Tyr Tyr Lys Thr Tyr Ala
    50                  55                  60

Asp Thr Val Arg Ala Ala Gly Leu Lys Trp Val Pro Ile Met Ser Thr
65                  70                  75                  80

His Ala Cys Gly Gly Asn Val Gly Asp Thr Val Asn Ile Pro Ile Pro
                85                  90                  95

Ser Trp Val Trp Thr Lys Asp Thr Gln Asp Asn Met Gln Tyr Lys Asp
            100                 105                 110

Glu Ala Gly Asn Trp Asp Asn Glu Ala Val Ser Pro Trp Tyr Ser Gly
        115                 120                 125

Leu Thr Gln Leu Tyr Asn Glu Phe Tyr Ser Ser Phe Ala Ser Asn Phe
    130                 135                 140

Ser Ser Tyr Lys Asp Ile Ile Thr Lys Ile Tyr Ile Ser Gly Gly Pro
145                 150                 155                 160
```

```
Ser Gly Glu Leu Arg Tyr Pro Ser Tyr Asn Pro Ser His Gly Trp Thr
            165                 170                 175

Tyr Pro Gly Arg Gly Ser Leu Gln Cys Tyr Ser Lys Ala Ala Ile Thr
            180                 185                 190

Ser Phe Gln Asn Ala Met Lys Ser Lys Tyr Gly Thr Ile Ala Ala Val
            195                 200                 205

Asn Ser Ala Trp Gly Thr Ser Leu Thr Asp Phe Ser Gln Ile Ser Pro
            210                 215                 220

Pro Thr Asp Gly Asp Asn Phe Phe Thr Asn Gly Tyr Lys Thr Thr Tyr
225                 230                 235                 240

Gly Asn Asp Phe Leu Thr Trp Tyr Gln Ser Val Leu Thr Asn Glu Leu
                245                 250                 255

Ala Asn Ile Ala Ser Val Ala His Ser Cys Phe Asp Pro Val Phe Asn
                260                 265                 270

Val Pro Ile Gly Ala Lys Ile Ala Gly Val His Trp Leu Tyr Asn Ser
            275                 280                 285

Pro Thr Met Pro His Ala Ala Glu Tyr Cys Ala Gly Tyr Tyr Asn Tyr
            290                 295                 300

Ser Thr Leu Leu Asp Gln Phe Lys Ala Ser Asn Leu Ala Met Thr Phe
305                 310                 315                 320

Thr Cys Leu Glu Met Asp Asp Ser Asn Ala Tyr Val Ser Pro Tyr Tyr
                325                 330                 335

Ser Ala Pro Met Thr Leu Val His Tyr Val Ala Asn Leu Ala Asn Asn
                340                 345                 350

Lys Gly Ile Val His Asn Gly Glu Asn Ala Leu Ala Ile Ser Asn Asn
            355                 360                 365

Asn Gln Ala Tyr Val Asn Cys Ala Asn Glu Leu Thr Gly Tyr Asn Phe
            370                 375                 380

Ser Gly Phe Thr Leu Leu Arg Leu Ser Asn Ile Val Asn Ser Asp Gly
385                 390                 395                 400

Ser Val Thr Ser Glu Met Ala Pro Phe Val Ile Asn Ile Val Thr Leu
                405                 410                 415

Thr Pro Asn Gly Thr Ile Pro Val Thr Phe Thr Ile Asn Asn Ala Thr
            420                 425                 430

Thr Tyr Tyr Gly Gln Asn Val Tyr Ile Val Gly Ser Thr Ser Asp Leu
            435                 440                 445

Gly Asn Trp Asn Thr Thr Tyr Ala Arg Gly Pro Ala Ser Cys Pro Asn
            450                 455                 460

Tyr Pro Thr Trp Thr Ile Thr Leu Asn Leu Leu Pro Gly Glu Gln Ile
465                 470                 475                 480

Gln Phe Lys Ala Val Lys Ile Asp Ser Ser Gly Asn Val Thr Trp Glu
                485                 490                 495

Gly Gly Ser Asn His Thr Tyr Thr Val Pro Thr Ser Gly Thr Gly Ser
            500                 505                 510

Val Thr Ile Thr Trp Gln Asn
            515

<210> SEQ ID NO 3
<211> LENGTH: 519
<212> TYPE: PRT
<213> ORGANISM: Artificial Sequence
<220> FEATURE:
<223> OTHER INFORMATION: Synthetic generation

<400> SEQUENCE: 3
```

```
Ser Ile Ala Pro Asn Phe Lys Val Phe Val Met Gly Pro Leu Glu Lys
1               5                   10                  15

Val Thr Asp Phe Asn Ala Phe Lys Asp Gln Leu Ile Thr Leu Lys Asn
            20                  25                  30

Asn Gly Val Tyr Gly Ile Thr Thr Asp Ile Trp Trp Gly Tyr Val Glu
            35                  40                  45

Asn Ala Gly Glu Asn Gln Phe Asp Trp Ser Tyr Tyr Lys Thr Tyr Ala
        50                  55                  60

Asp Thr Val Arg Ala Ala Gly Leu Lys Trp Val Pro Ile Met Ser Thr
65                  70                  75                  80

His Ala Ser Gly Gly Asn Val Gly Asp Thr Val Asn Ile Pro Ile Pro
                85                  90                  95

Ser Trp Val Trp Thr Lys Asp Thr Gln Asp Asn Met Gln Tyr Lys Asp
            100                 105                 110

Glu Ala Gly Asn Trp Asp Asn Glu Ala Val Ser Pro Trp Tyr Ser Gly
            115                 120                 125

Leu Thr Gln Leu Tyr Asn Glu Phe Tyr Ser Ser Phe Ala Ser Asn Phe
        130                 135                 140

Ser Ser Tyr Lys Asp Ile Ile Thr Lys Ile Tyr Ile Ser Gly Gly Pro
145                 150                 155                 160

Ser Gly Glu Leu Arg Tyr Pro Ser Tyr Asn Pro Ser His Gly Trp Thr
                165                 170                 175

Tyr Pro Gly Arg Gly Ser Leu Gln Cys Tyr Ser Lys Ala Ala Ile Thr
            180                 185                 190

Ser Phe Gln Asn Ala Met Lys Ser Lys Tyr Gly Thr Ile Ala Ala Val
        195                 200                 205

Asn Ser Ala Trp Gly Thr Ser Leu Thr Asp Phe Ser Gln Ile Ser Pro
210                 215                 220

Pro Thr Asp Gly Asp Asn Phe Phe Thr Asn Gly Tyr Lys Thr Thr Tyr
225                 230                 235                 240

Gly Asn Asp Phe Leu Thr Trp Tyr Gln Ser Val Leu Thr Asn Glu Leu
            245                 250                 255

Ala Asn Ile Ala Ser Val Ala His Ser Cys Phe Asp Pro Val Phe Asn
            260                 265                 270

Val Pro Ile Gly Ala Lys Ile Ser Gly Val His Trp Leu Tyr Asn Ser
        275                 280                 285

Pro Thr Met Pro His Ala Ala Glu Tyr Cys Ala Gly Tyr Tyr Asn Tyr
            290                 295                 300

Ser Thr Leu Leu Asp Gln Phe Lys Ala Ser Asn Leu Ala Met Ser Phe
305                 310                 315                 320

Thr Ser Leu Glu Met Asp Asp Ser Asn Ala Tyr Val Ser Pro Tyr Tyr
            325                 330                 335

Ser Ala Pro Met Thr Leu Val His Tyr Val Ala Asn Leu Ala Asn Asn
            340                 345                 350

Lys Gly Ile Val His Asn Gly Glu Asn Ala Leu Ala Ile Ser Asn Asn
        355                 360                 365

Asn Gln Ala Tyr Val Asn Cys Ala Asn Glu Leu Thr Gly Tyr Asn Phe
    370                 375                 380

Ser Gly Phe Thr Leu Leu Arg Leu Ser Asn Ile Val Asn Ser Asp Gly
385                 390                 395                 400

Ser Val Thr Ser Glu Met Ala Pro Phe Val Ile Asn Ile Val Thr Leu
            405                 410                 415
```

-continued

```
Thr Pro Asn Gly Thr Ile Pro Val Thr Phe Thr Ile Asn Asn Ala Thr
                420                 425                 430

Thr Tyr Tyr Gly Gln Asn Val Tyr Ile Val Gly Ser Thr Ser Asp Leu
        435                 440                 445

Gly Asn Trp Asn Thr Thr Tyr Ala Arg Gly Pro Ala Ser Cys Pro Asn
450                 455                 460

Tyr Pro Thr Trp Thr Ile Thr Leu Asn Leu Leu Pro Gly Glu Gln Ile
465                 470                 475                 480

Gln Phe Lys Ala Val Lys Ile Asp Ser Ser Gly Asn Val Thr Trp Glu
                485                 490                 495

Gly Gly Ser Asn His Thr Tyr Thr Val Pro Thr Ser Gly Thr Gly Ser
            500                 505                 510

Val Thr Ile Thr Trp Gln Asn
            515

<210> SEQ ID NO 4
<211> LENGTH: 519
<212> TYPE: PRT
<213> ORGANISM: Artificial Sequence
<220> FEATURE:
<223> OTHER INFORMATION: Synthetic generation

<400> SEQUENCE: 4

Ser Ile Ala Pro Asn Phe Lys Val Phe Val Met Gly Pro Leu Glu Lys
1               5                   10                  15

Val Thr Asp Phe Asn Ala Phe Lys Asp Gln Leu Ile Thr Leu Lys Asn
                20                  25                  30

Asn Gly Val Tyr Gly Ile Thr Thr Asp Ile Trp Trp Gly Tyr Val Glu
            35                  40                  45

Asn Ala Gly Glu Asn Gln Phe Asp Trp Ser Tyr Tyr Lys Thr Tyr Ala
        50                  55                  60

Asp Thr Val Arg Ala Ala Gly Leu Lys Trp Val Pro Ile Met Ser Thr
65                  70                  75                  80

His Ala Cys Gly Gly Asn Val Gly Asp Thr Val Asn Ile Pro Ile Pro
                85                  90                  95

Ser Trp Val Trp Thr Lys Asp Thr Gln Asp Asn Met Gln Tyr Lys Asp
                100                 105                 110

Glu Ala Gly Asn Trp Asp Asn Glu Ala Val Ser Pro Trp Tyr Ser Gly
            115                 120                 125

Leu Thr Gln Leu Tyr Asn Glu Phe Tyr Ser Ser Phe Ala Ser Asn Phe
        130                 135                 140

Ser Ser Tyr Lys Asp Ile Ile Thr Lys Ile His Ile Ser Gly Gly Pro
145                 150                 155                 160

Ser Gly Glu Leu Arg Tyr Pro Ser Tyr Asn Pro Ser His Gly Trp Thr
                165                 170                 175

Tyr Pro Gly Arg Gly Ser Leu Gln Cys Tyr Ser Lys Ala Ala Ile Thr
            180                 185                 190

Ser Phe Gln Asn Ala Met Lys Ser Lys Tyr Gly Thr Ile Ala Ala Val
        195                 200                 205

Asn Ser Ala Trp Gly Thr Ser Leu Thr Asp Phe Ser Gln Ile Ser Pro
    210                 215                 220

Pro Thr Asp Gly Asp Asn Phe Phe Thr Asn Gly Tyr Lys Thr Thr Tyr
225                 230                 235                 240

Gly Asn Asp Phe Leu Thr Trp Tyr Gln Ser Val Leu Thr Asn Glu Leu
                245                 250                 255
```

```
Ala Asn Ile Ala Ser Val Ala His Ser Cys Phe Asp Pro Val Phe Asn
            260                 265                 270

Val Pro Ile Gly Ala Lys Ile Ala Gly Val His Trp Leu His Asn Ser
        275                 280                 285

Pro Thr Met Pro His Ala Ala Glu Tyr Cys Ala Gly Tyr Tyr Asn Tyr
    290                 295                 300

Ser Thr Leu Leu Asp Gln Phe Lys Ala Ser Asn Leu Ala Met Thr Phe
305                 310                 315                 320

Thr Cys Leu Glu Met Asp Asp Ser Asn Ala Tyr Val Ser Pro Tyr Tyr
                325                 330                 335

Ser Ala Pro Met Thr Leu Val His Tyr Val Ala Asn Leu Ala Asn Asn
            340                 345                 350

Lys Gly Ile Val His Asn Gly Glu Asn Ala Leu Ala Ile Ser Asn Asn
        355                 360                 365

Asn Gln Ala Tyr Val Asn Cys Ala Asn Glu Leu Thr Gly Tyr Asn Phe
    370                 375                 380

Ser Gly Phe Thr Leu Leu Arg Leu Ser Asn Ile Val Asn Ser Asp Gly
385                 390                 395                 400

Ser Val Thr Ser Glu Met Ala Pro Phe Val Ile Asn Ile Val Thr Leu
                405                 410                 415

Thr Pro Asn Gly Thr Ile Pro Val Thr Phe Thr Ile Asn Asn Ala Thr
            420                 425                 430

Thr Tyr Tyr Gly Gln Asn Val Tyr Ile Val Gly Ser Thr Ser Asp Leu
        435                 440                 445

Gly Asn Trp Asn Thr Thr Tyr Ala Arg Gly Pro Ala Ser Cys Pro Asn
    450                 455                 460

Tyr Pro Thr Trp Thr Ile Thr Leu Asn Leu Pro Gly Glu Gln Ile
465                 470                 475                 480

Gln Phe Lys Ala Val Lys Ile Asp Ser Ser Gly Asn Val Thr Trp Glu
                485                 490                 495

Gly Gly Ser Asn His Thr Tyr Thr Val Pro Thr Ser Gly Thr Gly Ser
            500                 505                 510

Val Thr Ile Thr Trp Gln Asn
        515

<210> SEQ ID NO 5
<211> LENGTH: 551
<212> TYPE: PRT
<213> ORGANISM: Clostridium thermosulfurogenes

<400> SEQUENCE: 5

Met Ile Gly Ala Phe Lys Arg Leu Gly Gln Lys Leu Phe Leu Thr Leu
1               5                   10                  15

Leu Thr Ala Ser Leu Ile Phe Ala Ser Ser Ile Val Thr Ala Asn Ala
            20                  25                  30

Ser Ile Ala Pro Asn Phe Lys Val Phe Val Met Gly Pro Leu Glu Lys
        35                  40                  45

Val Thr Asp Phe Asn Ala Phe Lys Asp Gln Leu Ile Thr Leu Lys Asn
    50                  55                  60

Asn Gly Val Tyr Gly Ile Thr Thr Asp Ile Trp Trp Gly Tyr Val Glu
65                  70                  75                  80

Asn Ala Gly Glu Asn Gln Phe Asp Trp Ser Tyr Tyr Lys Thr Tyr Ala
                85                  90                  95

Asp Thr Val Arg Ala Ala Gly Leu Lys Trp Val Pro Ile Met Ser Thr
            100                 105                 110
```

-continued

His Ala Cys Gly Gly Asn Val Gly Asp Thr Val Asn Ile Pro Ile Pro
            115                 120                 125

Ser Trp Val Trp Thr Lys Asp Thr Gln Asp Asn Met Gln Tyr Lys Asp
130                 135                 140

Glu Ala Gly Asn Trp Asp Asn Glu Ala Val Ser Pro Trp Tyr Ser Gly
145                 150                 155                 160

Leu Thr Gln Leu Tyr Asn Glu Phe Tyr Ser Ser Phe Ala Ser Asn Phe
                165                 170                 175

Ser Ser Tyr Lys Asp Ile Ile Thr Lys Ile Tyr Ile Ser Gly Gly Pro
            180                 185                 190

Ser Gly Glu Leu Arg Tyr Pro Ser Tyr Asn Pro Ser His Gly Trp Thr
            195                 200                 205

Tyr Pro Gly Arg Gly Ser Leu Gln Cys Tyr Ser Lys Ala Ala Ile Thr
210                 215                 220

Ser Phe Gln Asn Ala Met Lys Ser Lys Tyr Gly Thr Ile Ala Ala Val
225                 230                 235                 240

Asn Ser Ala Trp Gly Thr Ser Leu Thr Asp Phe Cys Gln Ile Ser Pro
                245                 250                 255

Pro Thr Asp Gly Asp Asn Phe Phe Thr Asn Gly Tyr Lys Thr Thr Tyr
            260                 265                 270

Gly Asn Asp Phe Leu Thr Trp Tyr Gln Ser Val Leu Thr Asn Glu Leu
            275                 280                 285

Ala Asn Ile Ala Ser Val Ala His Ser Cys Phe Asp Pro Val Phe Asn
290                 295                 300

Val Pro Ile Gly Ala Lys Ile Ala Gly Val His Trp Leu Tyr Asn Ser
305                 310                 315                 320

Pro Thr Met Pro His Ala Ala Glu Tyr Cys Ala Gly Tyr Tyr Asn Tyr
                325                 330                 335

Ser Thr Leu Leu Asp Gln Phe Lys Ala Ser Asn Leu Ala Met Thr Phe
            340                 345                 350

Thr Cys Leu Glu Met Asp Asp Ser Asn Ala Tyr Val Ser Pro Tyr Tyr
            355                 360                 365

Ser Ala Pro Met Thr Leu Val His Tyr Val Ala Asn Leu Ala Asn Asn
            370                 375                 380

Lys Gly Ile Val His Asn Gly Glu Asn Ala Leu Ala Ile Ser Asn Asn
385                 390                 395                 400

Asn Gln Ala Tyr Val Asn Cys Ala Asn Glu Leu Thr Gly Tyr Asn Phe
                405                 410                 415

Ser Gly Phe Thr Leu Leu Arg Leu Ser Asn Ile Val Asn Ser Asp Gly
            420                 425                 430

Ser Val Thr Ser Glu Met Ala Pro Phe Val Ile Asn Ile Val Thr Leu
            435                 440                 445

Thr Pro Asn Gly Thr Ile Pro Val Thr Phe Thr Ile Asn Asn Ala Thr
450                 455                 460

Thr Tyr Tyr Gly Gln Asn Val Tyr Ile Val Gly Ser Thr Ser Asp Leu
465                 470                 475                 480

Gly Asn Trp Asn Thr Thr Tyr Ala Arg Gly Pro Ala Ser Cys Pro Asn
                485                 490                 495

Tyr Pro Thr Trp Thr Ile Thr Leu Asn Leu Pro Gly Glu Gln Ile
            500                 505                 510

Gln Phe Lys Ala Val Lys Ile Asp Ser Ser Gly Asn Val Thr Trp Glu
            515                 520                 525

```
Gly Gly Ser Asn His Thr Tyr Thr Val Pro Thr Ser Gly Thr Gly Ser
            530                 535                 540

Val Thr Ile Thr Trp Gln Asn
545                 550

<210> SEQ ID NO 6
<211> LENGTH: 518
<212> TYPE: PRT
<213> ORGANISM: Artificial Sequence
<220> FEATURE:
<223> OTHER INFORMATION: Synthetic generation

<400> SEQUENCE: 6

Ser Ile Ala Pro Asn Phe Lys Val Phe Val Met Gly Pro Leu Glu Lys
1               5                   10                  15

Val Thr Asp Phe Asn Ala Phe Lys Asp Gln Leu Ile Thr Leu Lys Asn
            20                  25                  30

Asn Gly Val Tyr Gly Ile Thr Thr Asp Ile Trp Trp Gly Tyr Val Glu
        35                  40                  45

Asn Ala Gly Glu Asn Gln Phe Asp Trp Ser Tyr Tyr Lys Thr Tyr Ala
    50                  55                  60

Asp Thr Val Arg Ala Ala Gly Leu Lys Trp Val Pro Ile Met Ser Thr
65                  70                  75                  80

His Ala Cys Gly Gly Asn Val Gly Asp Thr Val Asn Ile Pro Ile Pro
                85                  90                  95

Ser Trp Val Trp Thr Lys Asp Thr Gln Asp Asn Met Gln Tyr Lys Asp
            100                 105                 110

Glu Ala Gly Asn Trp Asp Asn Glu Ala Val Ser Pro Trp Tyr Ser Gly
        115                 120                 125

Leu Thr Gln Leu Tyr Asn Glu Phe Tyr Ser Ser Phe Ala Ser Asn Phe
    130                 135                 140

Ser Ser Tyr Lys Asp Ile Ile Thr Lys Ile Tyr Ile Ser Gly Gly Pro
145                 150                 155                 160

Ser Gly Glu Leu Arg Tyr Pro Ser Tyr Asn Pro Ser His Gly Trp Thr
                165                 170                 175

Tyr Pro Gly Arg Gly Ser Leu Gln Cys Tyr Ser Lys Ala Ala Ile Thr
            180                 185                 190

Ser Phe Gln Asn Ala Met Lys Ser Lys Tyr Gly Thr Ile Ala Ala Val
        195                 200                 205

Asn Ser Ala Trp Gly Thr Ser Leu Thr Asp Phe Ser Gln Ile Ser Pro
    210                 215                 220

Pro Thr Asp Gly Asp Asn Phe Phe Thr Asn Gly Tyr Lys Thr Thr Tyr
225                 230                 235                 240

Gly Asn Asp Phe Leu Thr Trp Tyr Gln Ser Val Leu Thr Asn Glu Leu
                245                 250                 255

Ala Asn Ile Ala Ser Val Ala His Ser Cys Phe Asp Pro Val Phe Asn
            260                 265                 270

Pro Ile Gly Ala Lys Ile Ala Gly Val His Trp Leu Tyr Asn Ser Pro
        275                 280                 285

Thr Met Pro His Ala Ala Glu Tyr Cys Ala Gly Tyr Tyr Asn Tyr Ser
    290                 295                 300

Thr Leu Leu Asp Gln Phe Lys Ala Ser Asn Leu Ala Met Thr Phe Thr
305                 310                 315                 320

Cys Leu Glu Met Asp Asp Ser Asn Ala Tyr Val Ser Pro Tyr Tyr Ser
                325                 330                 335
```

```
Ala Pro Met Thr Leu Val His Tyr Val Ala Asn Leu Ala Asn Asn Lys
            340                 345                 350

Gly Ile Val His Asn Gly Glu Asn Ala Leu Ala Ile Ser Asn Asn Asn
        355                 360                 365

Gln Ala Tyr Val Asn Cys Ala Asn Glu Leu Thr Gly Tyr Asn Phe Ser
    370                 375                 380

Gly Phe Thr Leu Leu Arg Leu Ser Asn Ile Val Asn Ser Asp Gly Ser
385                 390                 395                 400

Val Thr Ser Glu Met Ala Pro Phe Val Ile Asn Ile Val Thr Leu Thr
                405                 410                 415

Pro Asn Gly Thr Ile Pro Val Thr Phe Thr Ile Asn Asn Ala Thr Thr
            420                 425                 430

Tyr Tyr Gly Gln Asn Val Tyr Ile Val Gly Ser Thr Ser Asp Leu Gly
            435                 440                 445

Asn Trp Asn Thr Thr Tyr Ala Arg Gly Pro Ala Ser Cys Pro Asn Tyr
            450                 455                 460

Pro Thr Trp Thr Ile Thr Leu Asn Leu Pro Gly Glu Gln Ile Gln
465                 470                 475                 480

Phe Lys Ala Val Lys Ile Asp Ser Ser Gly Asn Val Thr Trp Glu Gly
                485                 490                 495

Gly Ser Asn His Thr Tyr Thr Val Pro Thr Ser Gly Thr Gly Ser Val
            500                 505                 510

Thr Ile Thr Trp Gln Asn
            515

<210> SEQ ID NO 7
<211> LENGTH: 551
<212> TYPE: PRT
<213> ORGANISM: Clostridium thermosulfurogenes

<400> SEQUENCE:

-continued

```
Ser Gly Glu Leu Arg Tyr Pro Ser Tyr Asn Pro Ser His Gly Trp Thr
        195                 200                 205
Tyr Pro Gly Arg Gly Ser Leu Gln Cys Tyr Ser Lys Ala Ala Ile Thr
        210                 215                 220
Ser Phe Gln Asn Ala Met Lys Ser Lys Tyr Gly Thr Ile Ala Ala Val
225                 230                 235                 240
Asn Ser Ala Trp Gly Thr Ser Leu Thr Asp Phe Ser Gln Ile Ser Pro
                245                 250                 255
Pro Thr Asp Gly Asp Asn Phe Phe Thr Asn Gly Tyr Lys Thr Thr Tyr
                260                 265                 270
Gly Asn Asp Phe Leu Thr Trp Tyr Gln Ser Val Leu Thr Asn Glu Leu
        275                 280                 285
Ala Asn Ile Ala Ser Val Ala His Ser Cys Phe Asp Pro Val Phe Asn
        290                 295                 300
Val Pro Ile Gly Ala Lys Ile Ala Gly Val His Trp Leu Tyr Asn Ser
305                 310                 315                 320
Pro Thr Met Pro His Ala Ala Glu Tyr Cys Ala Gly Tyr Tyr Asn Tyr
                325                 330                 335
Ser Thr Leu Leu Asp Gln Phe Lys Ala Ser Asn Leu Ala Met Thr Phe
        340                 345                 350
Thr Cys Leu Glu Met Asp Asp Ser Asn Ala Tyr Val Ser Pro Tyr Tyr
        355                 360                 365
Ser Ala Pro Met Thr Leu Val His Tyr Val Ala Asn Leu Ala Asn Asn
370                 375                 380
Lys Gly Ile Val His Asn Gly Glu Asn Ala Leu Ala Ile Ser Asn Asn
385                 390                 395                 400
Asn Gln Ala Tyr Val Asn Cys Ala Asn Glu Leu Thr Gly Tyr Asn Phe
                405                 410                 415
Ser Gly Phe Thr Leu Leu Arg Leu Ser Asn Ile Val Asn Ser Asp Gly
        420                 425                 430
Ser Val Thr Ser Glu Met Ala Pro Phe Val Ile Asn Ile Val Thr Leu
        435                 440                 445
Thr Pro Asn Gly Thr Ile Pro Val Thr Phe Thr Ile Asn Asn Ala Thr
        450                 455                 460
Thr Tyr Tyr Gly Gln Asn Val Tyr Ile Val Gly Ser Thr Ser Asp Leu
465                 470                 475                 480
Gly Asn Trp Asn Thr Thr Tyr Ala Arg Gly Pro Ala Ser Cys Pro Asn
                485                 490                 495
Tyr Pro Thr Trp Thr Ile Thr Leu Asn Leu Leu Pro Gly Glu Gln Ile
                500                 505                 510
Gln Phe Lys Ala Val Lys Ile Asp Ser Ser Gly Asn Val Thr Trp Glu
        515                 520                 525
Gly Gly Ser Asn His Thr Tyr Thr Val Pro Thr Ser Gly Thr Gly Ser
        530                 535                 540
Val Thr Ile Thr Trp Gln Asn
545                 550
```

BETA-AMYLASE ENZYMES

CROSS-REFERENCE TO RELATED APPLICATIONS

This application is a continuation of International Application No. PCT/IB2018/001276, filed Oct. 17, 2018, which claims the benefit of U.S. Provisional Application No. 62/576,930, filed Oct. 25, 2017.

SEQUENCE LISTING

This application includes a nucleotide and amino acid sequence listing in computer readable form (CRF) as an ASC II text (.txt) file according to "Standard for the Presentation of Nucleotide and Amino Acid Sequence Listings in International Patent Applications Under the Patent Cooperation Treaty (PCT)" ST.25. The sequence listing is identified below and is hereby incorporated by reference into the specification of this application in its entirety and for all purposes.

| File Name | Date of Creation | Size (bytes) |
|---|---|---|
| 170325 Sequence Listing.txt | Oct. 10, 2018 | 29.3 KB (30,022 bytes) |

TECHNICAL FIELD

Bread has been a staple of human nutrition for thousands of years. Bread is usually made by combining a flour, water, salt, yeast, and/or other food additives to make a dough or paste; then the dough is baked to make bread. Enzymes are known to be useful in baking because of the enzymes effects on the baking process may be similar or better than chemical alternatives. Several different enzymes may be used for making bread, for example amylase enzymes have been known to help maintain freshness over time (anti-stalling or hardness) and maintain resilience overtime. However, the baking industry still needs an amylase that may provide fresh bread over a longer time than what is currently available or an amylase enzyme that may provide bread that is better than fresh overtime. One solution to this problem is, the variant polypeptides having beta-amylase enzyme activity that meet or exceed these industrial requirements. In addition, the beta-amylase enzymes may be used in animal feed, detergents, personal care products, processing of textiles, pulp and paper processing, in the production of ethanol, in the production lignocellulosic ethanol, in the production of syrups, or as viscosity breakers in oilfield and mining industries.

BRIEF SUMMARY OF THE INVENTION

A variant polypeptide having beta-amylase activity, wherein the variant polypeptide is encoded by a nucleic acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to the nucleic acid sequence as set forth in SEQ ID NO:1.

A variant polypeptide having beta-amylase activity, wherein the variant polypeptide is selected from the group consisting of: (a) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:2, wherein the variant polypeptide has at least one single amino acid modification to the amino acid sequence of SEQ ID NO:2, at an amino acid residue position number: 16, 19, 24, 25, 27, 28, 48, 101, 105, 107, 119, 141, 143, 145, 146, 147, 153, 172, 175, 179, 197, 201, 203, 205, 206, 215, 219, 220, 221, 230, 364, 366, 369, 398, 399, 438, 440, 446, 452, 453, 456, 458, 463, 464, 465, 468, 476, 490, 499, 504, 508, or any combination thereof to the amino acid sequence of SEQ ID NO:2, and the variant polypeptide has beta-amylase activity; (b) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:3, wherein the variant polypeptide has at least one single amino acid modification to the amino acid sequence of SEQ ID NO:3, at an amino acid residue position number: 16, 19, 24, 25, 27, 28, 48, 83, 101, 105, 107, 119, 141, 143, 145, 146, 147, 153 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:3, and the variant polypeptide has beta-amylase activity; (b) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:4, wherein the variant polypeptide has at least one single amino acid modification to the amino acid sequence of SEQ ID NO:4, at an amino acid residue position number: 16, 19, 24, 25, 27, 28, 48, 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:4, and the variant polypeptide has beta-amylase activity; (d) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:5, wherein the variant polypeptide has at least one single amino acid modification to the amino acid sequence of SEQ ID NO:5, at an amino acid residue position number: 16, 19, 24, 25, 27, 28, 48 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:5, and the variant polypeptide has beta-amylase activity; (e) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:6, wherein the variant polypeptide has at least one single amino acid modification to the amino acid sequence of SEQ ID NO:6, at an amino acid residue position number: 16, 19, 24, 25, 27, 28, 48, 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:6, and the variant polypeptide has beta-amylase activity; and, (f) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:7, wherein the variant polypeptide has at least one single amino acid modification to the amino acid sequence of SEQ ID NO:7, at an amino acid residue position number: 48, 51, 56, 57, 59, 60, 80, 115, 133, 137, 139, 151, 173, 175, 177, 178, 179, 185, 187, 204, 207, 211, 229, 233, 235, 237, 238, 247, 251, 252, 253, 262, 305, 231, 318, 351, 354, 396, 398, 401, 430, 431, 470, 472, 478, 484, 485, 488, 490, 495, 496, 497, 500, 508, 522, 531, 536, 540, or any combination thereof to the amino acid sequence of SEQ ID NO:7, and the variant polypeptide has beta-amylase activity.

The variant polypeptides, wherein the at least one single amino acid modification is an amino acid substitution, insertion, deletion, or any combination thereof and the variant polypeptide has beta-amylase activity.

The variant polypeptides, wherein the amino acid substitution is a conservative amino acid substitution.

The variant polypeptides, wherein the at least one single amino acid modification is an amino acid substitution comprising: K16Q, D19I, D19L, K24D, K24E, D25P, L27Q, L27H, L27C, I28A, K48Q, E48D, D51I, D51L, K56D, K56E, D57P, D57K, L59Q, L59H, L59C, I60A, E80D, C83S, S83C, T101N, N107S, C115S, S115C, N119D, T133N, Q137L, N139S, A141R, N143D, S145N, S146P, Y147H, N151D, K153E, Y155H, H155Y, S172T, A173R, N175D, W175R, S177N, S178P, G179D, Y179H, K185E, Y187H, H187Y, A197T, K201E, G203I, S204T, I205M, A206H, W207R, G211D, S215D, F219W, S220W, S220C, C220S, C220L, C220W, Q221M, A229T, N230K, K233E, G235I, I237M, A238H, S247D, F251W, S252L, S252W, S252C, C252S, C252L, C252W, Q253M, N262K, N262G, V273*, A280S, S280A, H286Y, Y286H, V305*, A312S, S312A, Y318H, H318Y, T319S, S319T, C322S, S322C, T351S, S351T, C354S, S354C, A364P, S366H, N369P, A396P, S398H, S398P, D399M, N401P, S430P, D431M, N438Y, N738S, Y440N, S446P, N452D, T453K, A456S, G458D, P463T, P463L, N464D, Y465N, W468C, N470Y, N470S, Y472N, P476L, S478P, N484D, T485K, A488S, G490D, S490T, P495T, P495L, N496D, Y497N, S499P, W500C, T504N, P508L, S508T, S522T, S531P, T536N, S540T, or any combination thereof and the variant polypeptide has beta-amylase activity.

A variant polypeptide having beta-amylase activity, wherein the variant polypeptide is selected from the group consisting of: (i) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:2, wherein the variant polypeptide has a combination of amino acid modifications to the amino acid sequence of SEQ ID NO:2, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, S398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f2) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, P463L, Y465N, W468C; wherein the variant polypeptide has beta-amylase activity; (ii) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:3, wherein the variant polypeptide has a combination of amino acid modifications to the amino acid sequence of SEQ ID NO:3, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1)

D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, 5398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (l2) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (iii) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:4, wherein the variant polypeptide has a combination of amino acid modifications to the amino acid sequence of SEQ ID NO:4, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, 5398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, 5508T; (e2) D25K, A364P, N369P, S398P, T504N; (f2) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (iv) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:5, wherein the variant polypeptide has a combination of amino acid modifications to the amino acid sequence of SEQ ID NO:5, and the combination is selected from the group consisting of: (a1) D19I, L27C, A141R, A364P, N369P, S398P; (b1) D19I, L27C, I28A, S145N, G203I, C220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, C220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, C220L, A364P, N369P, 5398P; (n1) D25K, L27C, C220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, C220L, 5398P; (t1) K24E, L27H, I28A, C220L, A364P, N369P, S398P; (u1) N143D, A197T; (v1) C220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f2) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, C220L, A364P, N369P, S398P, K153E, K201E; (n2) D25K, L27C, C220L, A364P, N369P, S398P, E48D, N143Y, S146P, K201E; (o2) D25K, L27C, C220L, A364P, N369P, S398P, N107S, S172T, W175R; (p2) D25K, L27C, C220L, A364P, N369P, S398P, Q105L, N119D; (q2) D25K, L27C, C220L, A364P, N369P, S398P, P463T; (r2) D25K, L27C, C220L, A364P, N369P, S398P, N438Y, N464D, P476L; (s2) D25K, L27C, C220L, A364P, N369P, S398P, P463L, Y465N, W468C; (t2) D25K, L27C, K153E, K201E, C220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (vi) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:6, wherein the variant polypeptide has a combination of amino acid modifications to the amino acid sequence of SEQ ID NO:6, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, S398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f2) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (vii) the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:7, wherein the variant polypeptide has a combination of amino acid modifications to the amino acid sequence of SEQ ID NO:7, and the combination is selected from the group consisting of: (a1) D51I, L59C, A173R, A396P, N401P, S430P; (b1) D51I, L59C, I60A, S177N, G235I, S252L, A396P, N401P, S430P; (c1) D51I, L59H, Q253M; (d1) D57K, A396P, N401P, S430P; (e1) D57K, A396P, N401P, S430P; (f1) D57K, G235I, A396P, N401P, S430P; (g1) D57K, I60A, S252L, Q253M, A396P, N401P; (h1) D57K, L59C, G235I, A396P, N401P, S430P; (i1) D57K, L59C, G235I, A396P, N401P, S430P; (j1) D57K, L59C, G235I, Q253M, A396P, N401P, S430P; (k1) D57K, L59C, I60A, A173R, A396P, N401P, S430P; (l1) D57K, L59C, I60A, A173R, A396P, N401P, S430P; (m1) D57K, L59C, S177N, S252L, A396P, N401P, S430P; (n1) D57K, L59C, S252L, A396P, N401P, S430P; (o1) D57P, L59H, I60A, Q253M; (p1) G235I, A396P, N401P, S430P; (q1) K56E, D57K, L59C, A396P, N369P; (r1) K56E, D57K, L59C, I60A, A173R, A396P, N401P, S430P; (s1) K56E, D57P, L59H, A173R, G235I, S252L, S430P; (t) K56E, L59H, I60A, S252L, A396P, N401P, S430P; (u1) N175D, A229T; (v1) S252L, A396P, N401P, S430P; (w1) T133N, D431M; (x1) D57K, A396P, N401P, S430P, P495T; (y1) D57K, A396P, N401P, S430P, N470Y, N496D, P508L; (z1) D57K, A396P, N401P, S430P, P495L, Y497N, W500C; (a2) D57K, A396P, N401P, S430P, A488S; (b2) D57K, A396P, N401P, S430P, N470Y, Y472N; (c2) D57K, A396P, N401P, S430P, G490D; (d2) D57K, A396P, N401P, S430P, S540T; (e2) D57K, A396P, N401P, S430P, T540N; (f2) D57K, A396P, N401P, S430P, S522T; (g2) D57K, A396P, N401P, S430P, S531P; (h2) D57K, A396P, N401P, S430P, N484D; (i2) D57K, A396P, N401P, S430P, N470S; (j2) D57K, A396P, N401P, S430P, T485K; (k2) D57K, A396P, N401P, S430P, S478P; (l2) D57K, A396P, N401P, S430P, W500C; (m2) D57K, L59C, S252L, A396P, N401P, S430P, K185E, K233E; (n2) D57K, L59C, S252L, A396P, N401P, S430P, E48D, N175Y, S178P, K233E; (o2) D57K, L59C, S252L, A396P, N401P, S430P, N139S, S204T, W207R; (p2) D57K, L59C, S252L, A396P, N401P, S430P, Q137L, N151D; (q2) D57K, L59C, S252L, A396P, N401P, S430P, P495T; (r2) D57K, L59C, S252L, A396P, N401P, S430P, N470Y, N496D, P508L; (s2) D57K, L59C, S252L, A396P, N401P, S430P, P495L, Y497N, W500C; (t2) D57K, L59C, K185E, K233E, S252L, A396P, N401P, S430P, N470Y, N496D, P508L; (u2) D57K, L59C, G235I, Q253M, A396P, N401P, S430P, P495T; (v2) D57K, L59C, G235I, Q253M, A396P, N401P, S430P, N470Y, N496D, P508L; (w2) D57K, L59C, G235I, Q253M, A396P, N401P, S430P, P495L, Y497N, W500C; wherein the variant polypeptide has beta-amylase activity.

A variant polypeptide having beta-amylase activity, wherein the variant polypeptide is an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence as set forth in SEQ ID NO:2, and the variant polypeptide has an increase in enzyme activity, thermostability, pH-stability, or any combination thereof when compared to the beta-amylase of SEQ ID NO:2.

The variant polypeptides, wherein the variant polypeptide is a fragment of the full length amino acid sequence and the fragment has beta-amylase activity.

A variant polypeptide comprising a hybrid of at least one variant polypeptides, and a second polypeptide having amylase activity, wherein the hybrid has beta-amylase activity.

A composition comprising the variant polypeptides.

A composition comprising the variant polypeptides, and at least a second enzyme.

The composition comprising the variant polypeptides and at least a second enzyme, wherein the second enzyme is selected from the group consisting of: a second beta-amylase, a lipase, an alpha-amylase, a G4-amylase, a xylanase, a protease, a cellulase, a glucoamylase, an oxidoreductase, a phospholipase, and a cyclodextrin glucanotransferase.

A method of making the variant polypeptides comprising: providing a template nucleic acid sequence encoding the variant polypeptides, transforming the template nucleic acid sequence into an expression host, cultivating the expression host to produce the variant polypeptides, and purifying the variant polypeptide.

A method of making the variant polypeptides, wherein the template nucleic acid is the variant nucleotide of the nucleic acid sequence as set forth in SEQ ID NO:1, wherein the variant nucleotide is a nucleic acid sequence that is at least 80% identical to the nucleic acid sequence as set forth in SEQ ID NO:1, wherein the variant nucleotide encodes a polypeptide having beta-amylase activity.

A method of making the variant polypeptides, wherein the expression host is selected from the group consisting of: a bacterial expression system, a yeast expression system, a fungal expression system, and a synthetic expression system.

A method of making the variant polypeptides, wherein the bacterial expression system is selected from an *E. coli*, a *Bacillus*, a *Pseudomonas*, and a *Streptomyces*.

A method of making the variant polypeptides, wherein the yeast expression system is selected from a *Candida*, a *Pichia*, a *Saccharomyces*, a *Schizosaccharomyces*.

A method of making the variant polypeptides, wherein the fungal expression system is selected from a *Penicillium*, an *Aspergillus*, a *Fusarium*, a *Myceliopthora*, a *Rhizomucor*, a *Rhizopus*, a *Thermomyces*, and a *Trichoderma*.

A method of preparing a dough or a baked product prepared from the dough, the method comprising adding one of the variant polypeptides, to the dough and baking it. A method from preparing a dough or a baked product comprising: providing the variant polypeptides, providing a dough, contacting the variant polypeptide and the dough, and optionally baking the dough to generate a baked product.

A method of use of the variant polypeptides, for processing starch. A method of processing a starch comprising: providing the variant polypeptides, providing a starch, contacting the variant polypeptide and the starch, wherein the variant polypeptides hydrolyses the starch.

A method of use of the variant polypeptides, for cleaning or washing textiles, hard surfaces, or dishes. A method of for cleaning or washing textiles, hard surfaces, or dishes comprising: providing the variant polypeptides, providing a textile, hard surface, or dish, contacting the variant polypeptide and the textile, hard surface, or dish wherein the variant polypeptides cleans or washes the textile, hard surface, or dish.

A method of use of the variant polypeptides for making ethanol. A method for making ethanol comprising: providing the variant polypeptides, providing a feedstock, contacting the variant polypeptides and the feedstock, wherein the variant polypeptides hydrolyses the feedstock to a sugar, fomenting the sugar to generate ethanol.

A method of use of the variant polypeptides, for treating an oil well. A method for treating an oil well comprising: providing the variant polypeptides, providing an oil well fracturing fluid; contacting the variant polypeptide and the oil well fracturing fluid, wherein the variant polypeptide hydrolyses the oil fracturing fluid.

A method of use of the variant polypeptide as in any of claims 1-7, for processing pulp or paper comprising. A method for processing pulp or paper comprising: providing the variant polypeptides, providing a pulp or paper, contacting the variant polypeptides and the pulp or paper, wherein the variant polypeptide hydrolyses the pulp or paper.

A method of use of the variant polypeptide, for feeding an animal. A method for making an animal feed comprising: providing the variant polypeptides, providing an animal feed, contacting the variant polypeptide and the animal feed, wherein the variant polypeptide is part of the animal feed.

A method of use of the variant polypeptides, for making syrup. A method for making syrup comprising: providing the variant polypeptides, providing a sugar, contact the variant polypeptides and the sugar, wherein the variant polypeptides hydrolyses the sugar to generate a syrup.

DETAILED DESCRIPTION OF THE INVENTION

Figure 1:
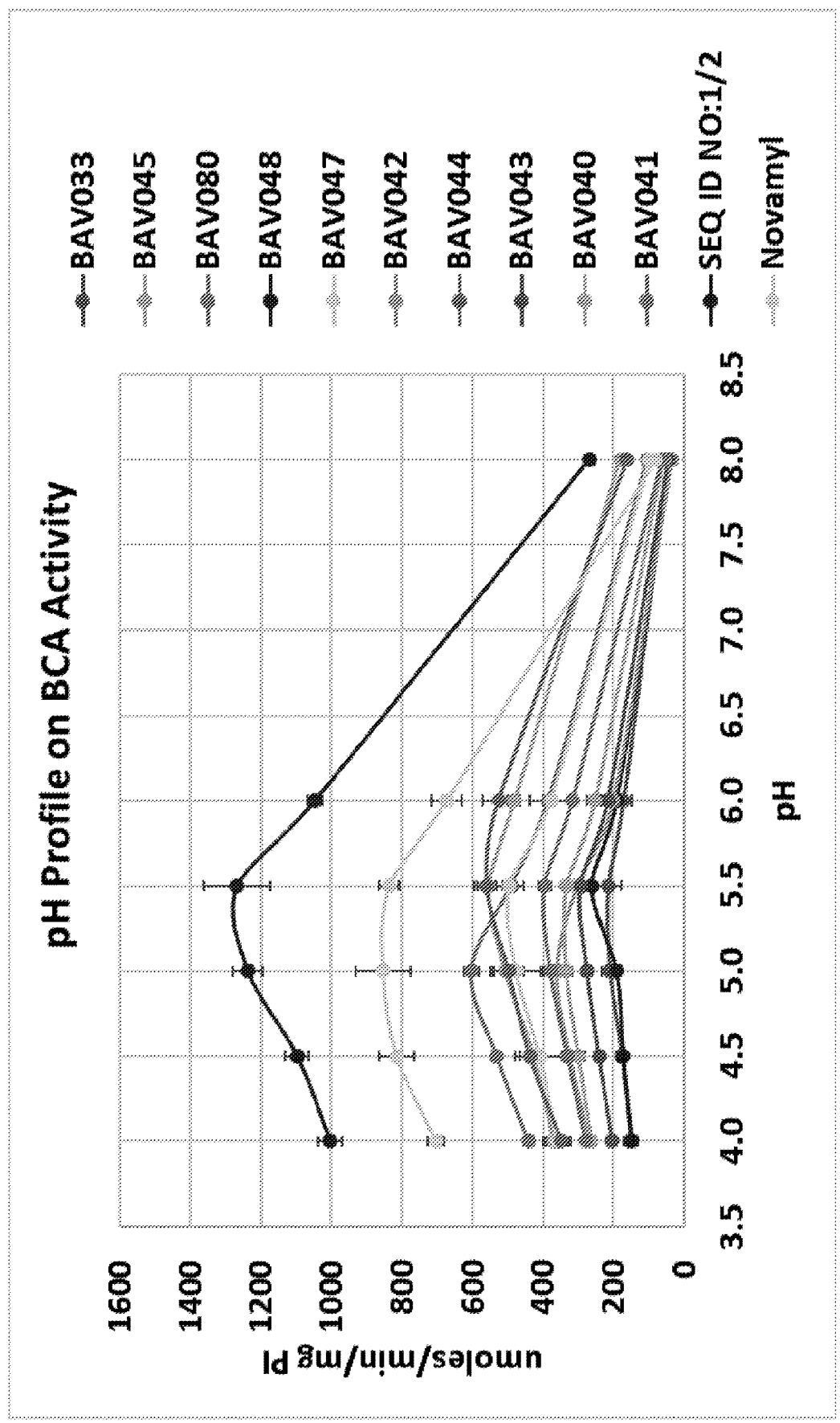
FIG. 1, shows the pH profiles for the variant beta-amylase enzymes.

An enzyme is a biological molecule comprising a sequence of amino acids, wherein the enzyme catalyzes a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also known as a polypeptide, a protein, a peptide, an amino acid sequence, or is identified by a SEQ ID NO. Alternative names for enzyme may be used interchangeably.

Different classes of enzymes are known to be useful in baking, including: Alpha-amylase (E.C. 3.2.1.1); Beta-amylase (3.2.1.2), Glucan 1,4-alpha-maltotetraohydrolase (E.C. 3.2.1.60), also known as exo-maltotetraohydrolase, G4-amylase; Glucan 1,4-alpha-maltohydrolase (E.C. 3.2.1.133), also known as maltogenic alpha-amylase; Endo-1,4-beta-xylanase (E.C. 3.2.1.8); Oxidoreductases; Phospholipase A1 (E.C. 3.1.1.32) Phospholipase A2 (E.C. 3.1.1.4); Phospholipase C (E.C. 3.1.4.3); Phospholipase D (E.C. 3.1.4.4); Galactolipase (E.C. 3.1.1.26), Cellulase (EC 3.2.1.4), Transglutaminases (EC 2.3.2.13), Phytase (EC 3.1.3.8; 3.1.3.26; and 3.1.1.72) and Protease. Enzymes are used as food ingredients, food additives, and/processing aids.

Beta-amylase (E.C. 3.2.1.2) preforms hydrolysis of (1->4)-alpha-D-glucosidic linkages in polysaccharides to remove successive maltose units from the non-reducing ends of the chains. Acts on starch, glycogen and related polysaccharides and oligosaccharides producing beta-maltose by an inversion. This enzyme is widely used in manufacturing caramel, maltose, maltodextrin and brewing beer, alcohol and vinegar fermentation industry. Beta-amylases are characterized in higher plants and microbial sources, for example beta-amylases from microbial sources are: *Bacillus acidopullulyticus* (U.S. Pat. No. 4,970,158), *Bacillus flexus* (Matsunaga, Okada and Yamagat, H. and Tsukagishi, N. 1987, J. Bacteriol. (169) 1564-1570), and U.S. Pat. No. 8,486,682. Other beta-amylases from microbial sources are: *Clostridium thermosulfurogenes* (Kitaoto, 1988, Kitamoto, N., Yamagata, H., Kato, T., Tsukagoshi, N. and Udaka, S. 1998. J. Bacteriol. (170) 5848-5854), U.S. Patent Application Publication 2012/0225164, WO2015/021600, WO2015/021601, EP0337090A1 and *Thermoanaerobacterium thermosulfurigenes* JP01218589. Based on the beta-amylase originated from *Clostridium thermosulfurogenes* acid-resistant beta-amylases were developed (CN103695386 and CN 103881993).

In addition, amylase enzymes are disclosed in patents and published patent applications including: WO2002/068589, WO2002/068597, WO2003/083054, WO2004/042006, WO2008/080093, WO2013/116175, and WO2017/106633.

Commercial amylase enzymes used in food processing and baking including: Veron® from AB Enzymes; BakeDream®, BakeZyme®, and Panamore® available from DSM; POWERSoft®, Max-LIFE™, POWERFlex®, and POWERFresh® available from DuPont; and Fungamyl®, Novamyl®, OptiCake®, and Sensea® available from Novozymes.

Lipases (E.C. 3.1.1.3) are hydrolytic enzymes that are known to cleave ester bonds in lipids. Lipases include phospholipases, triacylglycerol lipases, and galactolipases. Lipases have been identified from plants; mammals; and microorganisms including but not limited to: *Pseudomonas, Vibrio, Acinetobacter, Burkholderia, Chromobacterium*, Cutinase from *Fusarium solani* (FSC), *Candida antarctica* A (CalA), *Rhizopus oryzae* (ROL), *Thermomyces lanuginosus* (TLL), *Rhizomucor miehei* (RML), *Aspergillus Niger, Fusarium heterosporum, Fusarium oxysporum, Fusarium culmorum* lipases.

In addition, many lipases, phospholipases, and galactolipases have been disclosed in patents and published patent applications including, but not limited to: WO1993/000924, WO2003/035878, WO2003/089620, WO2005/032496, WO2005/086900, WO2006/031699, WO2008/036863, and WO2011/046812.

Commercial lipases used in food processing and baking including, but not limited to: LIPOPAN™, NOOPAZYME, LIPOPAN MAX, LIPOPAN Xtra (available from Novozymes); PANAMORE, CAKEZYME, and BAKEZYME (available from DSM); and GRINDAMYL EXEL 16, GRINDAMYL POWERBAKE, and TS-E 861 (available from Dupont/Danisco).

A "parent" polypeptide amino acid sequence is the starting sequence for introduction of mutations (e.g. by introducing one or more amino acid substitutions, insertions, deletions, or a combination thereof) to the sequence, resulting in "variants" of the parent polypeptide amino acid sequences. A parent includes: A wild-type polypeptide amino acid sequence or synthetically generated polypeptide amino acid sequence that is used as starting sequence for introduction of (further) changes.

A "variant polypeptide" refers to an enzyme that differs from its parent in its amino acid sequence. Variant polypeptides, are described using the nomenclature and abbreviations for single amino acid molecules according to the recommendations of IUPAC for single letter or three letter amino acid abbreviations.

"Substitutions" are described by providing the original amino acid followed by the number of the position within the amino acid sequence. For example, a substitution of amino acid residue 24, means that the amino acid of the parent at position 24, can be substituted with any of the 19 other amino acid residues. In addition, a substitution can be described by providing the original amino acid followed by the number of the position within the amino acid sequence and followed by the specific substituted amino acid. For example, the substitution of histidine at position 120 with alanine is designated as "His120Ala" or "H120A". Combinations of substitutions, are described by inserting comas between the amino acid residues, for example: K24E, D25P, L27H, A141R, G203I, S220L, S398P; represent a combination of seven different amino acid residues substitutions when compared to a parent polypeptide. Variants having substitutions in the context of amino acid changes, may also be applied to nucleic acid modifications, e.g. by substitutions.

Variant polypeptides having an amino acid substitution, wherein the substitution may be a conservative amino acid substitution. A "conservative amino acid substitution" or related amino acid" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue. A list of related amino acids is given in the Table below (see for example Creighton (1984) Proteins. W.H. Freeman and Company (Eds)). Examples of conserved amino acid substitutions:

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |

-continued

| Residue | Conservative Substitutions |
|---------|---------------------------|
| Phe | Met; Leu; Tyr |
| Ser | Thr; Gly |
| Thr | Ser; Val |
| Trp | Tyr |
| Tyr | Trp; Phe |
| Val | Ile; Leu |

WIPO Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code apply. A compilation of such non-standard code translation tables is maintained at the NCBI.

| Amino Acids | | | |
|-------------|--|--|--|
| Name | 3 letter codes | 1 letter code | Nucleic Acids DNA codons |
| Alanine | Ala | A | GCA, GCC, GCG, GCT |
| Arginine | Arg | R | AGA, AGG, CGA, CGC, CGG, CGT |
| Asparagine | Asn | N | AAC, AAT |
| Aspartic acid; (Aspartate) | Asp | D | GAC, GAT |
| Cysteine | Cys | C | TGC, TGT |
| Glutamic acid; (Glutamate) | Glu | E | GAA, GAG |
| Glutamine | Gln | Q | CAA, CAG |
| Glycine | Gly | G | GGA, GGC, GGG, GGT |
| Histidine | His | H | CAC, CAT |
| Isoleucine | Ile | I | ATA, ATC, ATT |
| Leucine | Leu | L | CTA, CTC, CTG, CTT, TTA, TTG |
| Lysine | Lys | K | AAA, AAG |
| Methionine | Met | M | ATG |
| Phenylalanine | Phe | F | TTC, TTT |
| Proline | Pro | P | CCA, CCC, CCG, CCT |
| Serine | Ser | S | AGC, AGT, TCA, TCC, TCG, TCT |
| Threonine | Thr | T | ACA, ACC, ACG, ACT |
| Tryptophan | Trp | W | TGG |
| Tyrosine | Tyr | Y | TAC TAT |
| Valine | Val | V | GTA, GTC, GTG, GTT |

The variant polypeptides having beta-amylase activity may be a "mature polypeptide." A mature polypeptide means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, etc.

Enzymatic activity changes during storage or operational use of the enzyme. The term "enzyme stability" relates to the retention of enzymatic activity as a function of time during storage or operation.

To determine and quantify changes in catalytic activity of enzymes stored or used under certain conditions over time, the "initial enzymatic activity" is measured under defined conditions at time cero (100%) and at a certain point in time later (x %). By comparison of the values measured, a potential loss of enzymatic activity can be determined in its extent. The extent of enzymatic activity loss determines an enzymes stability or non-stability.

Parameters influencing the enzymatic activity of an enzyme and/or storage stability and/or operational stability are for example pH, temperature, and presence of oxidative substances:

The variant polypeptides may be active over a broad pH at any single point within the range from about pH 4.0 to about pH 12.0. The variant polypeptides having beta-amylase activity are active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. The variant polypeptides having beta-amylase enzyme activity is active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, and higher.

"pH stability", refers to the ability of a protein to function over a specific pH range. In general, most enzymes are working under conditions with rather high or rather low pH ranges.

Variant polypeptides may be active over a broad temperature used in at any time during a baking process, wherein the temperature is any point in the range from about 20° C. to about 60° C. The variant polypeptides having beta-amylase enzyme activity are active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides having beta-amylase enzyme activity are active at a temperature of at least 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C. ° C., 42° C. ° C., 43° C. ° C., 44° C. ° C., 45° C. ° C., 46° C. ° C., 47° C. ° C., 48° C. ° C., 49° C. ° C., 50° C. ° C., 51° C. ° C., 52° C., 53° C., 54° C., 55° C., 56° C., 57° C., 58° C., 59° C., 60° C., 61° C., 62° C., or higher temperatures.

"Thermal stability" and "thermostability" refer to the ability of a protein to function over a temperature range. In general, most enzymes have a finite range of temperatures at which they function. In addition to enzymes that work in mid-range temperatures (e.g., room temperature), there are enzymes that are capable of working in very high or very low temperatures. Thermostability is characterized by what is known as the $T_{50}$ value (also called half-life, see above). The $T_{50}$ indicates the temperature at which 50% residual activity is still present after thermal inactivation for a certain time compared with a reference sample which has not undergone thermal treatment.

"Thermal tolerance" and "thermotolerance" refer to the ability of a protein to function after exposure to a specific temperature, such as a very high or very low temperature. A thermotolerant protein may not function at the exposure temperature, but will function once returned to a favorable temperature.

"Purified" means that the material is in a relatively pure state, e.g., at least about 90% pure, at least about 95% pure, or at least about 98% or 99% pure. Preferably "purified" means that the material is in a 100% pure state.

A "synthetic" or "artificial" compound is produced by in vitro chemical or enzymatic synthesis. The variant nucleic acids can be generated with optimal codon usage for host organisms, such as a yeast cell host or other expression hosts of choice or variant protein sequences with amino acid modifications, such as e.g. substitutions, compared to the parent protein sequence, e.g. to optimize properties of the polypeptide.

The term "non-naturally occurring" refers to a (poly) nucleotide, amino acid, (poly)peptide, enzyme, protein, cell, organism, or other material that is not present in its original environment or source, although it may be initially derived from its original environment or source and then reproduced non-naturally occurring processes under laboratory conditions.

"Sequence Identity," "% sequence identity," "% identity," or "Sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both, mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The differences between these two approaches, counting gaps as non-identical positions vs ignoring gaps, at a single position can lead to variability in sequence identity value between two sequences.

A sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

A sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

A sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

A sequence alignment is calculated with mismatches at a single position are counted as non-identical positions in final sequence identity calculation; however, gaps at a single position are not counted (ignored) as non-identical positions in final sequence identity calculation. The sequence alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used with the programs default parameter (gap open=10.0, gap extend=0.5 and matrix=EBLOSUM62). Then, a sequence identity can be calculated from the alignment showing both sequences over the full length, so showing the first sequence and the second sequence in their full length ("Global sequence identity"). For example: % sequence identity=(# of identical residues/length of alignment)×100)].

The variant polypeptides are described as an amino acid sequence which is at least n % identical to the amino acid sequence of the respective parent enzyme with "n" being an integer between 10 and 100. The variant polypeptides include enzymes that are at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical when compared to the full length amino acid sequence of the parent enzyme, wherein the enzyme variant has enzymatic activity. A "Fragment", or "subsequence" as used herein are a portion of a polynucleotide or an amino acid sequence. The fragments or subsequences may retain or encode for at least one functional activity of the sequence to which it is related.

"Functional fragment" refers to any nucleic acid or amino acid sequence which comprises merely a part of the full length nucleic acid or full length amino acid sequence, respectively, but still has the same or similar activity and/or function. The fragment comprises at least 70%, at least 80%, at least 85%, at least 90%, at least 95%, at least 96%, at least 97%, at least 98%, at least 99% of the original sequence. The functional fragment comprises contiguous nucleic acids or amino acids compared to the original nucleic acid or original amino acid sequence, respectively.

The variant polypeptides having beta-amylase activity may be a hybrid of more than one beta-amylase enzyme. A "hybrid" or "chimeric" or "fusion protein" means that a domain of a first variant polypeptides beta-amylase is combined with a domain of a second beta-amylase to form a hybrid amylase and the hybrid has amylase activity. A domain of variant polypeptides having beta amylase enzyme activity can be combined with a domain of a commercially available amylase, such as Veron® from AB Enzymes; BakeDream®, BakeZyme®, and Panamore® available from DSM; POWERSoft®, Max-LIFE™, POWERFlex®, and POWERFresh® available from DuPont; and Fungamyl®, Novamyl®, OptiCake®, and Sensea® available from Novozymes. In addition, domains from various amylase enzymes can be recombined into a single enzyme, wherein the enzyme has amylase activity.

Industrial enzymes are usually recombinant proteins produced using bacteria, fungi, or yeast expression systems. "Expression system" also means a host microorganism, expression hosts, host cell, production organism, or production strain and each of these terms can be used interchangeably. Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis*, or *Bacillus licheniformis, Pseudomonas*, preferably *Pseudomonas fluorescens, Pichia pastoris* (also known as *Komiagataella phaffii*), *Myceliopthora thermophile* (C1), *Schizosaccharomyces pombe, Trichoderma*, preferably *Trichoderma reesei* and *Saccharomyces*, preferably *Saccharomyces cerevisiae*. The variant polypeptides having beta-amylase enzyme activity are produced using the expression system listed above.

The term "heterologous" (or exogenous or foreign or recombinant) polypeptide is: (a) a polypeptide that is not native to the host cell. The protein sequence of such a heterologous polypeptide is a synthetic, non-naturally occurring, "man made" protein sequence; (b) a polypeptide native to the host cell in which structural modifications, e.g., deletions, substitutions, and/or insertions, have been made to alter the native polypeptide; or (c) a polypeptide native to the host cell whose expression is quantitatively altered or whose expression is directed from a genomic location different from the native host cell as a result of manipulation of the DNA of the host cell by recombinant DNA techniques, e.g., a stronger promoter.

The term "heterologous" (or exogenous or foreign or recombinant) polynucleotide refers: (a) to a polynucleotide that is not native to the host cell; (b) a polynucleotide native to the host cell in which structural modifications, e.g., deletions, substitutions, and/or insertions, have been made to alter the native polynucleotide; (c) a polynucleotide native to the host cell whose expression is quantitatively altered as a result of manipulation of the regulatory elements of the polynucleotide by recombinant DNA techniques, e.g., a stronger promoter; or (d) a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences do not occur naturally in the specific combination with each other.

"Vector" means any kind of construct suitable to carry foreign polynucleotide sequences for transfer to another cell, or for stable or transient expression within a given cell. The term "vector" encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence, which may be referred to as a "gene of interest." The gene of interest may comprise introns and exons, depending on the kind of origin or destination of host cell.

The variant nucleotide of the nucleic acid sequence as set forth in SEQ ID NO:1, wherein the variant nucleotide is a nucleic acid sequence that is at least 80% identical to the nucleic acid sequence as set forth in SEQ ID NO:1, wherein the variant nucleotide encodes an enzyme variant polypeptide having beta-amylase activity.

A method of making the variant polypeptides having beta-amylase enzyme activity comprises: providing a template nucleic acid sequence wherein the template nucleic acid is a variant nucleotide of the nucleic acid sequence as set forth in SEQ ID NO:1, wherein the variant nucleotide is a nucleic acid sequence that is at least 80% identical to the nucleic acid sequence as set forth in SEQ ID NO:1, wherein the variant nucleotide encodes a polypeptide having beta-amylase activity.

Transforming the template nucleic acid sequence into an expression host Cultivating the expression host to produce the variant polypeptide, and purifying the variant polypeptide.

The template nucleic acid is a variant nucleotide of the nucleic acid sequence as set forth in SEQ ID NO:1, wherein the variant nucleotide is a nucleic acid sequence that is at least 80% identical to the nucleic acid sequence as set forth in SEQ ID NO:1, wherein the variant nucleotide encodes a polypeptide having beta-amylase activity.

The polypeptide variants having beta-amylase enzyme activity may be used or formulated alone or as a mixture of enzymes.

The formulation may be a solid form such as powder, a lyophilized preparation, a granule, a tablet, a bar, a crystal, a capsule, a pill, a pellet, or in a liquid form such as in an aqueous solution, an aerosol, a gel, a paste, a slurry, an aqueous/oil emulsion, a cream, a capsule, or in a vesicular or micellar suspension.

The variant polypeptides having beta-amylase enzyme activity may be used in combination with at least one other enzyme. The other enzyme may be from the same class of enzymes, for example, a composition comprising a first beta-amylase and a second beta-amylase. The other enzyme may also be from a different class of enzymes, for example, a composition comprising the variant polypeptides having beta-amylase enzyme activity and a lipase. The combination with at least one other enzyme may be a composition comprising at least three enzymes. The three enzymes may have enzymes from the same class of enzymes, for example a first amylase, a second amylase, and a third amylase; or the enzymes may be from different class of enzymes for example, the variant polypeptides having beta-amylase enzyme activity, a lipase, and a xylanase.

The second enzyme comprises: an alpha-amylase; a beta-amylase, a Glucan 1,4-alpha-maltotetraohydrolase, also known as exo-maltotetraohydrolase, G4-amylase; a Glucan 1,4-alpha-maltohydrolase, also known as maltogenic alpha-amylase, a cyclodextrin glucanotransferase, a glucoamylase; an Endo-1,4-beta-xylanase; a xylanase, a cellulase, an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a protease, or any combination thereof. The enzyme combination is the variant polypeptides having beta-amylase enzyme activity and a lipase, or the enzyme combination is the beta-amylase, a lipase, and a xylanase.

The variant polypeptides having beta-amylase enzyme activity may be in a composition. The composition comprising the variant polypeptides having beta-amylase enzyme activity.

The composition comprises the variant polypeptides having beta-amylase enzyme activity as and a second enzyme.

Preferably the second enzyme is selected from the group consisting of: a second beta-amylase, a lipase, an alpha-amylase, a G4-amylase, a xylanase, a protease, a cellulase, a glucoamylase, an oxidoreductase, a phospholipase, and a cyclodextrin glucanotransferase.

The composition may be used in the preparation of bakery products.

The variant polypeptides having beta-amylase enzyme activity may be used in a method of preparing a dough or a beaked product prepared from the dough, the method comprising adding one of the variant enzymes to the dough and baking it.

Bread includes, but is not limited to: rolls, buns, pastries, cakes, flatbreads, pizza bread, pita bread, wafers, pie crusts naan, lavish, pitta, focaccia, sourdoughs, noodles, cookies, deep-fired (doughnuts) tortillas, pancakes, crepes, croutons, and biscuits. The bread could also be an edible container such as a cup or a cone. Baking bread generally involves mixing ingredients to form dough, kneading, rising, shaping, baking, cooling and storage. The ingredients used for making dough generally include flour, water, salt, yeast, and other food additives.

Flour is generally made from wheat and may be milled for different purposes such as making bread, pastries, cakes, biscuits pasta, and noodles. Alternatives to wheat flour include, but are not limited to: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof. Flour type is known to vary between different regions and different countries around the world.

Treatment of flour or dough, may include adding inorganic substances, organic substances such as fatty acids, carbohydrates, amino acids, proteins, and nuts. The flour or dough may be pretreated prior to baking by cooling, heating, irradiation, agglomeration, or freeze-drying. In addition, the flour or dough may be pretreated prior to baking by adding enzymes, or microorganisms, such as yeasts.

Yeast breaks down sugars into carbon dioxide and water. A variety of Baker's yeast, which are usually derived from *Saccharomyces cerevisiae*, are known to those skilled in the art including, but not limited to: cream yeast, compressed yeast, cake yeast, active dry yeast, instant yeast, osmotolerant yeasts, rapid-rise yeast, deactivated yeast. Other kinds of yeast include nutritional yeast, brewer's yeast, distiller's and wine yeast.

Sweeteners include but are not limited to: liquid sugar, syrups, white (granulated) sugars, brown (raw) sugars, honey, fructose, dextrose, glucose, high fructose corn syrup, molasses, and artificial sweeteners.

Emulsifiers include but are not limited to diacetyl tartaric acid esters of monoglycerides (DATEM), sodium stearoyl lactylate (SSL), calcium stearoyl lactylate (CSL), ethoxylated mono- and diglycerides (EMG), polysorbates (PS), and succinylated monoglycerides (SMG).

Other food additives may be used with the methods of baking include: Lipids, oils, butter, margarine, shortening, butterfat, glycerol, eggs, diary, non-diary alternatives, thickeners, preservatives, colorants, and enzymes.

Ingredients or additives for baking may be added individually to during the baking process. The ingredients or additives may also be combined with more than one ingredient or additive to form pre-mixes and then the pre-mixes are added during the baking process. The flour or dough mixtures may be prepared prior to baking including ready-for oven doughs, packaged doughs or packaged batters.

Bakery products may be modified to meet special dietary requirements such as sugar-free, gluten-free, low fat, or any combination thereof. The enzymes may extend shelf-life of a dough-based product or provide antimicrobial (mold-free) effects.

Variant polypeptides having beta-amylase enzyme activity may be useful for other industrial applications. The variant polypeptides having beta-amylase enzyme activity are used in a detergent, a personal care product, in the processing of textiles, in pulp and paper processing, in the production of ethanol, lignocellulosic ethanol, or syrups; as viscosity breakers in oilfield and mining industries.

"Baked products" includes baked products such as bread, crispy rolls, sandwich bread, buns, baguette, ciabatta, croissants, noodles, as well as fine bakery wares like donuts, brioche, stollen, cakes, muffins, etc.

"Dough" is defined as a mixture of flour, salt, yeast and water, which may be kneaded, molded, shaped or rolled prior to baking. In addition, also other ingredients such as sugar, margarine, egg, milk, etc. might be used. The term includes doughs used for the preparation of baked goods, such as bread, rolls, sandwich bread, baguette, ciabatta, croissants, sweet yeast doughs, etc.

"Bread volume" is the volume of a baked good determined by using a laser scanner (e.g. Volscan Profiler ex Micro Stable System) to measure the volume as well as the specific volume. The term also includes the volume which is determined by measuring the length, the width and the height of certain baked goods.

The description in range format is merely for convenience and brevity and should not be construed as an inflexible limitation on the scope of the disclosure. Accordingly, the description of a range is considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present disclosure will become apparent from the following specifications taken in conjunction with the accompanying drawings.

In the following description, numerous specific details are set forth to provide a more thorough understanding of the present disclosure. However, it will be apparent to one of skill in the art that the methods of the present disclosure may be practiced without one or more of these specific details. In other instances, well-known features and procedures well known to those skilled in the art have not been described to avoid obscuring the disclosure.

Example 1: PAHBAH Assay

Quantitation of starch hydrolysis for the beta-amylase and variant enzymes was measured using the 4-Hydroxybenzhydrazide method as described in Lever M. (1972) "A new reaction for colorimetric determination of carbohydrates." Anal. Biochem. 47, 273-279, with the following modifications. 112 uL of 1% potato amylopectin was reacted with 12.5 uL of diluted enzyme at 65° C. and samples taken at 10 minutes. The reaction was then quenched by mixing into 100 ul 1% PAHBAH reagent. The reaction was heated to 95° C. for 6 minutes, cooled to room temperature, and the solution absorption was read at 410 nm in a BioTek plate reader.

Example 2: Residual Activity

Residual activity was calculated by comparing the activity of each enzyme as measured using the PAHBAH assay before and after a heat challenge at 82° C. or 88° C. After heating the sample for 10 minutes at 82° C. or 88° C., the sample was cooled to room temperature before being tested, using the PAHBAH assay, at 65° C.

Example 3: ThermoFluor Assay

The melting point (Tm) for each beta-amylase enzyme variant was measured in a high throughput manner using the ThermoFluor assay as described in Lo, M C; Aulabaugh, A; Jin, G; Cowling, R; Bard, J; Malamas, M; Ellestad, G (1 Sep. 2004). "Evaluation of fluorescence-based thermal shift assays for hit identification in drug discovery" Analytical Biochemistry 332 (1): 153-9.:10.1016/j.ab.2004.04.031, PMID 15301960, with the following modifications. A 50 ul reaction in 50 mM Na Acetate pH6, 5×SYPRO orange and enzyme supernatant was subjected to at heat ramp from 50° C. to 98° C. at 1° C. per minute. The dye fluorescence was monitored using in a BioRad CFX 384 real time PCR machine. The melt curve data was analyzed using the supplied CFX Manager Software.

Example 4: Expression of Variant Beta-Amylase

The variant polypeptides having beta-amylase activity were obtained by constructing expression plasmids containing the encoding polynucleotide sequences, transforming plasmids into *Pichia pastoris* (*Komagataella phaffii*) and growing the resulting expression strains in the following way. Fresh *Pichia pastoris* cells of the expression strains were obtained by spreading the glycerol stocks of sequence-confirmed strains onto Yeast extract Peptone Dextrose (YPD) agar plates containing Zeocin. After 2 days, starter seed cultures of the production strains were inoculated into 100 mL of Buffered Glycerol complex Medium (BMGY) using cells from these plates, and grown for 20-24 hours at 30° C. and 225-250 rpm. Seed cultures were scaled up by transferring suitable amounts into 2-4 L of BMMY medium in a baffled Fermenter. Fermentations were carried out at 30° C. and under 1100 rpm of agitation, supplied via flat-blade impellers, for 48-72 hours. After the initial batch-phase of fermentation, sterile-filtered Methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

The variant polypeptides having beta-amylase amylase were identified as follows: supernatant was assayed for protein of interest expression by either SDS-PAGE or capillary electrophoresis.

Example 5: Variant Beta-Amylase Enzymes

A parent enzyme was selected from KITAMOTO, "Cloning and Sequencing of the Gene Encoding Thermophilic B-amylase of *Clostridium thermosulfurogenes*" (1988) J. Bacteriology Vol. 170, p. 5848-5854; NCBI_P19584.1 is AAA23204.1, and is identified in this application as the amino acid sequence of SEQ ID NO:2, which is encoded by the nucleic acid sequence SEQ ID NO.:1. The parent enzyme was engineered in the lab to generate non-naturally occurring beta-amylase variant enzymes having improve characteristics of the enzyme. The improved characteristics, include thermostability, pH, enzyme activity, or any combination thereof.

The variant polypeptide enzymes were created starting with the parent enzyme and evolving it using Gene Site Saturation Mutagenesis (GSSM) of the parent enzyme as described in at least U.S. Pat. Nos. 6,562,594, 6,171,820, and 6,764,835; Error Prone PCR; and/or Tailored Multi-Site-Combinatorial Assembly (TMSCA), as described in U.S. Pat. No. 9,476,078.

The beta-amylase variant enzymes may be an amino acid insertion, deletion, or substitution when compared to the parent enzyme. The substitutions may be one amino acid residue for a different amino acid; the substitutions may be conservative amino acid substitutions, or the substitutions may be a similar amino acid residue. In addition, the substitutions may be at more than one site in the amino acid sequence. For example, a beta-amylase variant may have at least two amino acid substitutions wherein the substitutions are at amino acid residues 143 and 197. In addition, multiple substitutions may be made to the parent enzyme. For example, a beta-amylase variant may have amino acid substitutions at amino acid residue numbers 203, 364, 369, and 398. Additional examples the structural changes to the amino acid sequence of the parent enzyme and having single point amino acid substitutions or combinations of amino acid substitutions, and the functional improvements of the variant polypeptides having improved enzyme activity, thermostability, pH, and any combination thereof when compared to the parent enzyme are shown below in Table 1.

TABLE 1

| Tm (° C.) | PAHBAH at 65° C. | PAHBAH Residual Activity at 65° C. | % Residual | Code | Enzymes |
| --- | --- | --- | --- | --- | --- |
| 77-78 | 1.491 | 0.777 | 52.100 | SEQ ID NO: 1/2 | Parent Beta Amylase |
| 78.0 | 1.087 | 0.736 | 67.70 | BAV023 | A141R |
| 79.0 | 1.050 | 0.794 | 75.60 | BAV006 | A206H |
| 79.5 | 1.008 | 0.655 | 65.00 | BAV026 | A364P |
| 78.0 | 0.887 | 0.622 | 70.10 | BAV018 | D19I |
| 86.0 | 0.247 | 0.269 | 108.90 | BAV052 | D19I, L27C, A141R, A364P, N369P, S398P |
| 85.0 | | | | BAV050 | D19I, L27C, I28A, S145N, G203I, S220L, A364P, N369P, S398P |

TABLE 1-continued

| Tm (° C.) | PAHBAH at 65° C. | PAHBAH Residual Activity at 65° C. | % Residual | Code | Enzymes |
|---|---|---|---|---|---|
| 85.0 | 0.295 | 0.291 | 98.60 | BAV036 | D19I, L27H, Q221M |
| 78.5 | 1.044 | 0.711 | 68.10 | BAV021 | D19L |
| 78.0 | 1.336 | 0.796 | 59.60 | BAV032 | D25K |
| 84.0 | 3.644 | 3.238 | 88.90 | BAV045 | D25K, A364P, N369P, S398P |
| 91.0 | 0.310 | 0.305 | 98.39 | BAV054 | D25K, A364P, N369P, S398P, A456S |
| 85.0 | 0.539 | 0.308 | 57.14 | BAV055 | D25K, A364P, N369P, S398P, N438S |
| 86.0 | 0.530 | 0.344 | 64.91 | BAV056 | D25K, A364P, N369P, S398P, N438Y, N464D, P476L |
| 84.0 | 0.317 | 0.303 | 95.58 | BAV057 | D25K, A364P, N369P, S398P, N438Y, Y440N |
| 85.0 | 0.646 | 0.322 | 49.85 | BAV058 | D25K, A364P, N369P, S398P, N452D |
| 86.0 | 0.597 | 0.343 | 57.45 | BAV059 | D25K, A364P, N369P, S398P, P463L, Y465N, W468C |
| 85.0 | 0.519 | 0.330 | 63.58 | BAV060 | D25K, A364P, N369P, S398P, P463T |
| 85.0 | 0.532 | 0.300 | 56.39 | BAV061 | D25K, A364P, N369P, S398P, S446P |
| 85.0 | 0.599 | 0.317 | 52.92 | BAV062 | D25K, A364P, N369P, S398P, S490T |
| 86.0 | 0.591 | 0.305 | 51.61 | BAV063 | D25K, A364P, N369P, S398P, S499P |
| 85.0 | 0.586 | 0.326 | 55.63 | BAV064 | D25K, A364P, N369P, S398P, S508T |
| 84.0 | 0.561 | 0.303 | 54.01 | BAV065 | D25K, A364P, N369P, S398P, T453K |
| 85.0 | 0.599 | 0.323 | 53.92 | BAV066 | D25K, A364P, N369P, S398P, T504N |
|  | 0.561 | 0.309 | 55.08 | BAV067 | D25K, A364P, N369P, S398P, W468C |
| 85.0 | 0.311 | 0.317 | 101.93 | BAV068 | D25K, A364P, N369P, S398P, G458D |
| 84.0 | 3.499 | 2.094 | 59.80 | BAV042 | D25K, G203I, A364P, N369P, S398P |
| 83.0 | 3.414 | 1.596 | 46.70 | BAV044 | D25K, I28A, S220L, Q221M, A364P, N369P |
| 85.0 | 3.519 | 2.091 | 59.40 | BAV048 | D25K, L27C, G203I, A364P, N369P, S398P |
| 85.0 | 3.385 | 2.524 | 74.60 | BAV046 | D25K, L27C, G203I, A364P, N369P, S398P |
| 84.0 | 3.364 | 2.289 | 68.00 | BAV040 | D25K, L27C, G203I, Q221M, A364P, N369P, S398P |
| 87.0 |  |  |  | BAV069 | D25K, L27C, G203I, Q221M, A364P, N369P, S398P, N438Y, N464D, P476L |
| 86.0 |  |  |  | BAV070 | D25K, L27C, G203I, Q221M, A364P, N369P, S398P, P463L, Y465N, W468C |
| 86.0 |  |  |  | BAV071 | D25K, L27C, G203I, Q221M, A364P, N369P, S398P, P463T |
| 85.0 | 2.568 | 1.232 | 48.00 | BAV041 | D25K, L27C, I28A, A141R, A364P, N369P, S398P |
| 86.0 |  |  |  | BAV072 | D25K, L27C, K153E, K201E, S220L, A364P, N369P, S398P, N438Y, N464D, P476L |
| 85.0 |  |  |  | BAV049 | D25K, L27C, S145N, S220L, A364P, N369P, S398P |
| 84.0 | 3.561 | 2.392 | 67.20 | BAV047 | D25K, L27C, S220L, A364P, N369P, S398P |
| 86.0 | 0.691 | 0.343 | 0.50 | BAV073 | D25K, L27C, S220L, A364P, N369P, S398P, E48D, N143Y, S146P, K201E |
| 86.0 | 0.483 | 0.328 | 0.68 | BAV074 | D25K, L27C, S220L, A364P, N369P, S398P, K153E, K201E |
| 86.0 |  |  |  | BAV075 | D25K, L27C, S220L, A364P, N369P, S398P, N438Y, N464D, P476L |
| 86.0 |  |  |  | BAV076 | D25K, L27C, S220L, A364P, N369P, S398P, P463L, Y465N, W468C |
| 87.0 |  |  |  | BAV077 | D25K, L27C, S220L, A364P, N369P, S398P, P463T |
| 86.0 | 0.850 | 0.325 | 0.38 | BAV078 | D25K, L27C, S220L, A364P, N369P, S398P, N107S, S172T, W175R |
| 86.0 | 0.986 | 0.402 | 0.41 | BAV079 | D25K, L27C, S220L, A364P, N369P, S398P, Q105L, N119D |
| 78.5 | 1.364 | 0.837 | 61.40 | BAV029 | D25P |
| 83.0 | 3.421 | 2.331 | 68.10 | BAV037 | D25P, L27H, I28A, Q221M |
| 78.5 | 1.505 | 1.054 | 70.00 | BAV019 | F219W |
| 80.0 | 1.238 | 0.893 | 72.10 | BAV011 | G179D |
| 79.5 | 1.127 | 0.773 | 68.60 | BAV020 | G203I |
| 85.0 | 2.164 | 1.261 | 58.30 | BAV033 | G203I, A364P, N369P, S398P |
| 79.5 | 1.537 | 1.012 | 65.80 | BAV024 | I205M |
| 78.0 | 1.294 | 0.913 | 70.60 | BAV014 | I28A |
| 78.5 | 1.252 | 0.890 | 71.10 | BAV012 | K16Q |
| 78.5 | 1.582 | 1.111 | 70.20 | BAV017 | K24D |
| 79.0 | 2.038 | 1.308 | 64.20 | BAV027 | K24E |
| 84.0 | 3.282 | 2.135 | 65.10 | BAV034 | K24E, D25K, L27C, A364P, N369P |
| 84.0 | 3.486 | 1.746 | 50.10 | BAV043 | K24E, D25K, L27C, I28A, A141R, A364P, N369P, S398P |

TABLE 1-continued

| Tm (° C.) | PAHBAH at 65° C. | PAHBAH Residual Activity at 65° C. | % Residual | Code | Enzymes |
|---|---|---|---|---|---|
| 84.0 | 3.281 | 1.815 | 55.30 | BAV035 | K24E, D25P, L27H, A141R, G203I, S220L, S398P |
| 89.0 | 0.645 | 0.323 | 50.10 | BAV051 | K24E, L27H, I28A, S220L, A364P, N369P, S398P |
| 79.0 | 2.215 | 1.329 | 60.00 | BAV030 | L27C |
| 79.0 | 2.146 | 1.317 | 61.40 | BAV028 | L27H |
| 80.0 | 1.585 | 1.078 | 68.00 | BAV022 | L27Q |
| 78.0 | 1.108 | 0.830 | 74.90 | BAV008 | N143D, A197T |
| 78.5 | 1.278 | 0.931 | 72.80 | BAV010 | N230G |
| 78.5 | 0.927 | 0.785 | 84.70 | BAV001 | N230K |
| 79.5 | 1.074 | 0.801 | 74.60 | BAV009 | N369P |
| 80.0 | 1.086 | 0.854 | 78.60 | BAV003 | Q221M |
| 80.0 | 0.991 | 0.789 | 79.60 | BAV002 | S145N |
| 79.0 | 1.083 | 0.813 | 75.10 | BAV007 | S215D |
| 79.0 | 1.498 | 1.176 | 78.50 | BAV004 | S220L |
| 84.0 | 3.281 | 1.815 | 55.30 | BAV080 | K24D, D25K, L27C, A141R, 203I, 220L, 398P |
| 79.0 | 1.270 | 0.963 | 75.80 | BAV005 | S220W |
| 79.5 | 1.311 | 0.924 | 70.50 | BAV015 | S398P |
| 79.0 | 1.336 | 0.798 | 59.70 | BAV031 | T101N, D399M |

Example 6: pH of Variant Beta-Amylase Enzymes

The variant polypeptides having beta-amylase activity and the pH profile of the enzymes was determined using BCA Assay: substrate is 1% Amylopectin from Potato (Sigma No. A8515 Lot # SLBS5819); reaction buffer is 50 mM Britton Robinson Buffer, 125 µL total; lyo-powder enzyme; diluted enzyme 12.54; wavelengths read 560 nm; pH 4.0, 4.5, 5.0, 5.5, 6.0, 8.0 at 60° C. Pre-warm up to 10 PCR strip/tubes in thermocycler for 10 minutes prior to starting reactions. Incubate 112.5 µl (buffer) in PCR: 1% amylopectin in any given buffer for minimum 10 minutes at appropriate temperature. Initiate reaction by addition of 12.5 µL of enzyme dilution. At each time point (TP), take 10 uL aliquot of reaction into BCA solution plate. Once all time points have been taken, heat BCA Stop plate at 80° C. for 30 minutes, cool. Transfer 100 µL of developed BCA solution into 96 well flat bottom plates and read at 560 nm. The results are shown in the Table 2 below and FIG. 1.

TABLE 2

| | Average Activity (umoles/min/mg PI) | | | | | |
|---|---|---|---|---|---|---|
| pH | 4.0 | 4.5 | 5.0 | 5.5 | 6.0 | 8.0 |
| BAV033 | 150.80 | 176.20 | 210.45 | 215.00 | 171.66 | 45.03 |
| STDEV | 20.35 | 15.01 | 23.77 | 38.73 | 21.63 | 7.04 |
| % CV | 13% | 9% | 11% | 18% | 13% | 16% |
| BAV045 | 371.14 | 427.36 | 509.57 | 556.13 | 482.64 | 181.13 |
| STDEV | 19.14 | 8.29 | 30.50 | 41.18 | 16.62 | 7.70 |
| % CV | 5% | 2% | 6% | 7% | 3% | 4% |
| BAV080 | 442.22 | 531.31 | 603.87 | 491.23 | 385.64 | 103.76 |
| STDEV | 11.98 | 2.94 | 21.26 | 14.68 | 11.50 | 13.25 |
| % CV | 3% | 1% | 4% | 3% | 3% | 13% |
| BAV048 | 148.80 | 172.37 | 191.81 | 262.82 | 191.49 | 38.41 |
| STDEV | 3.15 | 7.88 | 6.11 | 9.85 | 5.22 | 0.32 |
| % CV | 2% | 5% | 3% | 4% | 3% | 1% |
| BAV047 | 359.84 | 410.10 | 476.78 | 495.99 | 379.22 | 97.83 |
| STDEV | 38.65 | 68.28 | 72.04 | 40.38 | 58.17 | 9.68 |
| % CV | 11% | 17% | 15% | 8% | 15% | 10% |
| BAV042 | 268.32 | 324.06 | 360.52 | 302.56 | 200.29 | 34.88 |
| STDEV | 17.56 | 12.36 | 21.38 | 6.66 | 1.58 | 2.92 |
| % CV | 7% | 4% | 6% | 2% | 1% | 8% |
| BAV044 | 348.15 | 438.30 | 498.37 | 559.53 | 527.09 | 161.34 |
| STDEV | 18.43 | 27.21 | 44.68 | 26.41 | 44.21 | 10.79 |
| % CV | 5% | 6% | 9% | 5% | 8% | 7% |

TABLE 2-continued

| BAV043 | 203.15 | 241.20 | 274.37 | 294.25 | 215.85 | 44.83 |
|---|---|---|---|---|---|---|
| STDEV | 13.35 | 5.82 | 14.83 | 30.14 | 22.47 | 2.40 |
| % CV | 7% | 2% | 5% | 10% | 10% | 5% |
| BAV040 | 263.34 | 301.49 | 336.22 | 335.50 | 253.16 | 57.40 |
| STDEV | 7.65 | 18.71 | 19.43 | 4.40 | 22.38 | 5.38 |
| % CV | 3% | 6% | 6% | 1% | 9% | 9% |
| BAV041 | 278.95 | 330.32 | 379.03 | 395.83 | 316.24 | 61.60 |
| STDEV | 8.95 | 13.93 | 19.95 | 17.17 | 7.29 | 3.19 |
| % CV | 3% | 4% | 5% | 4% | 2% | 5% |
| SEQ ID NO: 1/2 | 1003.47 | 1097.86 | 1238.28 | 1268.50 | 1047.73 | 268.32 |
| STDEV | 32.37 | 32.44 | 42.82 | 92.78 | 22.19 | 13.53 |
| % CV | 3% | 3% | 3% | 7% | 2% | 5% |
| Novamyl | 703.54 | 814.39 | 854.24 | 835.15 | 672.98 | 80.22 |
| STDEV | 23.87 | 48.19 | 77.26 | 28.99 | 42.98 | 3.90 |
| % CV | 3% | 6% | 9% | 3% | 6% | 5% |

| | Average Activity (umoles/min/mg PI) | | | | | |
|---|---|---|---|---|---|---|
| pH | 4.00 | 4.50 | 5.00 | 5.50 | 6.00 | 8.00 |
| BAV060 | | | | | | |
| AVE | 271.09 | 319.97 | 371.70 | 430.31 | 399.33 | 147.46 |
| STDEV | 8.11 | 14.36 | 20.38 | 33.07 | 21.57 | 1.31 |
| % CV | 3% | 4% | 5% | 8% | 5% | 1% |
| BAV056 | | | | | | |
| AVE | 189.45 | 221.94 | 264.66 | 292.57 | 285.27 | 107.90 |
| STDEV | 7.72 | 10.13 | 0.58 | 9.39 | 23.57 | 7.12 |
| % CV | 4% | 5% | 0% | 3% | 8% | 7% |
| BAV059 | | | | | | |
| AVE | 347.96 | 378.26 | 447.60 | 468.55 | 440.46 | 166.12 |
| STDEV | 60.91 | 15.79 | 17.18 | 34.31 | 20.25 | 5.56 |
| % CV | 18% | 4% | 4% | 7% | 5% | 3% |
| BAV077 | | | | | | |
| AVE | 477.46 | 571.91 | 659.24 | 757.52 | 744.22 | 263.73 |
| STDEV | 28.70 | 19.05 | 40.57 | 71.75 | 74.19 | 10.66 |
| % CV | 6% | 3% | 6% | 9% | 10% | 4% |
| BAV075 | | | | | | |
| AVE | 297.89 | 415.19 | 491.89 | 565.78 | 517.82 | 189.21 |
| STDEV | 48.56 | 24.18 | 35.62 | 10.37 | 50.58 | 11.13 |
| % CV | 16% | 6% | 7% | 2% | 10% | 6% |

TABLE 2-continued

| | | | | | | |
|---|---|---|---|---|---|---|
| BAV076 | | | | | | |
| AVE | 290.95 | 359.50 | 441.15 | 455.22 | 463.10 | 154.72 |
| STDEV | 22.08 | 15.32 | 21.13 | 7.80 | 14.15 | 4.13 |
| % CV | 8% | 4% | 5% | 2% | 3% | 3% |
| BAV072 | | | | | | |
| AVE | 124.25 | 124.60 | 117.88 | 106.99 | 85.15 | 14.74 |
| STDEV | 5.42 | 11.41 | 7.97 | 8.35 | 7.60 | 0.66 |
| % CV | 4% | 9% | 7% | 8% | 9% | 4% |
| BAV071 | | | | | | |
| AVE | 491.42 | 597.73 | 703.85 | 790.79 | 769.04 | 292.66 |
| STDEV | 24.45 | 22.77 | 14.27 | 34.83 | 52.61 | 16.46 |
| % CV | 5% | 4% | 2% | 4% | 7% | 6% |
| BAV069 | | | | | | |
| AVE | 292.24 | 367.09 | 434.66 | 470.03 | 448.89 | 171.38 |
| STDEV | 13.96 | 6.43 | 17.21 | 12.89 | 18.92 | 10.41 |
| % CV | 5% | 2% | 4% | 3% | 4% | 6% |
| BAV070 | | | | | | |
| AVE | 268.43 | 340.00 | 398.54 | 477.03 | 432.18 | 137.77 |
| STDEV | 54.63 | 64.93 | 101.11 | 97.79 | 98.30 | 25.40 |
| % CV | 20% | 19% | 25% | 21% | 23% | 18% |

Example 7: Baking for Wheat Pan Bread

The baking performance of the variant polypeptides having beta-amylase activity were tested in wheat pan bread produced in a straight process. 1000 g of flour type 550 (Vogtmühlen Illertissen), 30 g compressed yeast, 20 g salt, 20 g sugar, 20 g margarine, 60 ppm ascorbic acid, 150 ppm Nutrilife® CS 30 (fungal xylanase, cellulase, fungal alpha-amylase), 8 g Nutrisoft® 55 (distilled monoglyceride) and 580 g water was mixed in a Kemper SP 15 spiral mixer for 4.5 minutes at speed 1 and 2.25 minutes at speed 2, to a final dough temperature of 28° C. After a resting of 15 minutes, the dough was divided into 500 g pieces, rounded and proofed for 15 minutes. Afterwards the dough pieces were molded, given into a baking tin and proofed for 80 minutes at 35° C. at relative humidity of 85%. The proofed dough pieces were baked in a deck oven for 25 minutes at 255° C./240° C. under and upper heat, with 15 seconds steam injection.

The variant polypeptide enzyme samples were added to the flour at dosages from 27 ppm to 325 ppm. The effects on the dough properties and on the final baked goods, were compared to a negative control (no enzyme), Novamyl 10,000, and to Novamyl 3D.

The volume effect was determined by measuring the bread loafs via a laser scanner (Stable Micro Systems VolScan Profiler, VolScan 600). The negative control is defined as 0%. Dough properties were evaluated haptically by a skilled master baker and described in comparison to the negative control.

Figure 2:
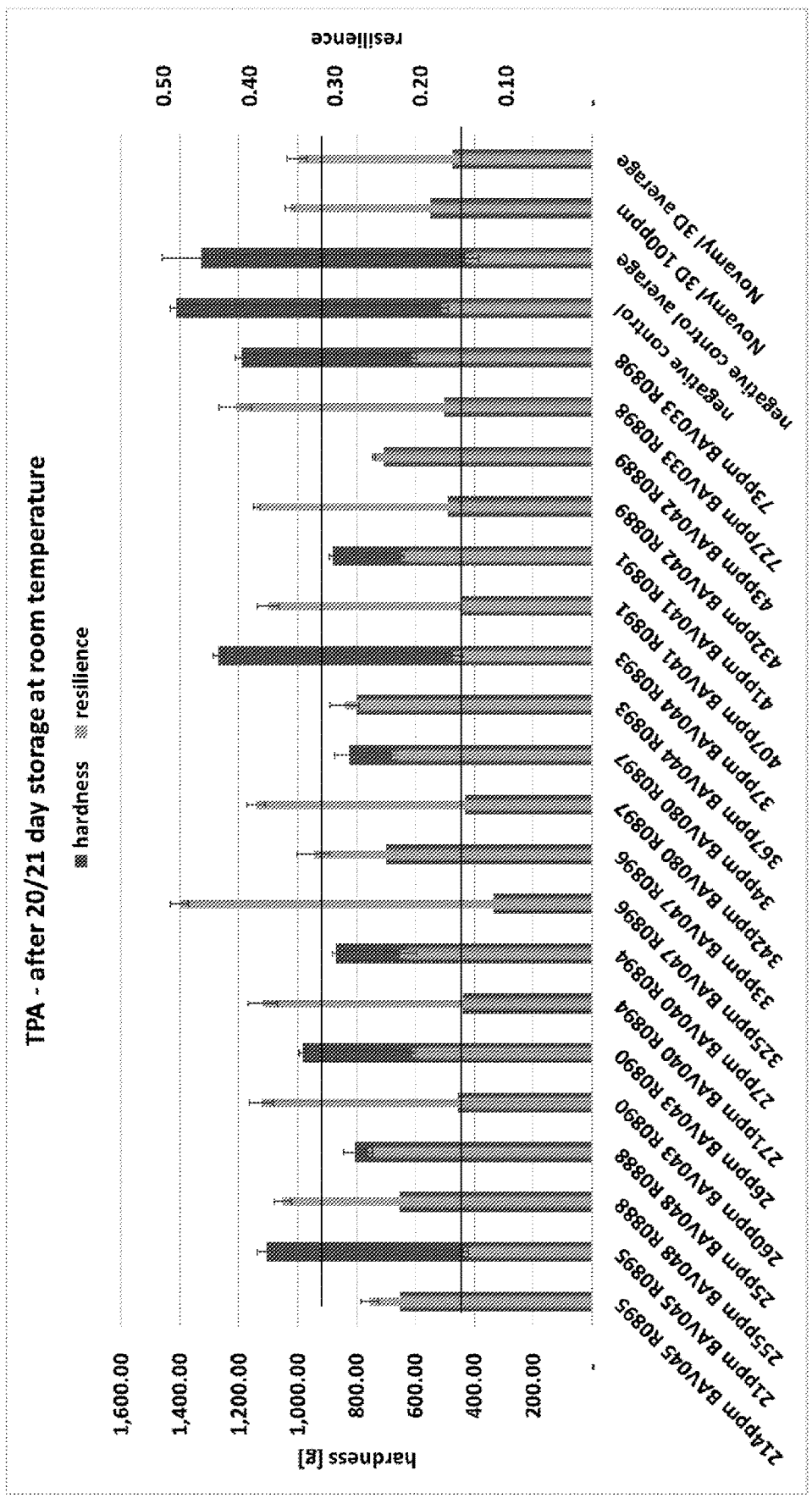
FIG. 2, shows the results for hardness and resilience of bread for a 20-day trial.

The ready baked breads were packed and sealed in a plastic bag. In addition, they partly were pasteurized for 90 minutes at 85° C. Fresh and after defined storage times, typically after 1, 10, 20 days, the effect on crumb properties was determined by texture profile analyses by using a texture analyzer (Stable Micro Systems, TA.XTplus Texture Analyzer). Therefore, 25-millimeter-thick slices were cut out of the middle of the bread loafs, prior to the measurement. The results are shown below in table 3, and in FIG. 2.

TABLE 3

| Dosage (ppm) Enzyme | hardness | resilience | S.D. hardness | S.D. resilience |
|---|---|---|---|---|
| 214 ppm BAV045 R0895 | 650.57 | 0.26 | 6.00 | 0.01 |
| 21 ppm BAV045 R0895 | 1,105.60 | 0.15 | 32.40 | 0.01 |
| 255 ppm BAV048 R0888 | 653.93 | 0.36 | 40.47 | 0.01 |
| 25 ppm BAV048 R0888 | 805.91 | 0.26 | 39.47 | 0.00 |
| 260 ppm BAV043 R0890 | 453.84 | 0.39 | 27.58 | 0.01 |
| 26 ppm BAV043 R0890 | 983.35 | 0.21 | 10.68 | 0.00 |
| 271 ppm BAV040 R0894 | 437.86 | 0.38 | 4.34 | 0.02 |
| 27 ppm BAV040 R0894 | 870.00 | 0.22 | 11.78 | 0.02 |
| 325 ppm BAV047 R0896 | 335.89 | 0.48 | 1.66 | 0.01 |
| 33 ppm BAV047 R0896 | 697.79 | 0.33 | 2.41 | 0.02 |
| 342 ppm BAV080 R0897 | 430.79 | 0.39 | 18.98 | 0.01 |
| 34 ppm BAV080 R0897 | 825.39 | 0.23 | 50.14 | 0.00 |
| 367 ppm BAV044 R0893 | 797.85 | 0.29 | 20.85 | 0.02 |
| 37 ppm BAV044 R0893 | 1,267.04 | 0.16 | 20.03 | 0.01 |
| 407 ppm BAV041 R0891 | 440.73 | 0.38 | 1.49 | 0.01 |
| 41 ppm BAV041 R0891 | 881.07 | 0.22 | 11.16 | 0.00 |
| 432 ppm BAV042 R0889 | 488.20 | 0.39 | 4.15 | 0.00 |
| 43 ppm BAV042 R0889 | 709.00 | 0.25 | 4.82 | 0.00 |
| 727 ppm BAV033 R0898 | 501.86 | 0.42 | 10.93 | 0.02 |
| 73 ppm BAV033 R0898 | 1,190.74 | 0.21 | 22.09 | 0.01 |
| negative control | 1,412.01 | 0.18 | 19.55 | 0.01 |
| negative control average | 1,327.44 | 0.15 | 134.06 | 0.02 |
| Novamyl 3D 100 ppm | 548.21 | 0.35 | 13.13 | 0.01 |
| Novamyl 3D average | 473.58 | 0.34 | 46.20 | 0.01 |

What is claimed is:

1. A variant polypeptide having beta-amylase activity, wherein the variant polypeptide is selected from the group consisting of:

(a) variant polypeptide is an amino acid sequence that is at least 95% identical to the amino acid sequence as set forth in SEQ ID NO:2, wherein the variant polypeptide has at least one single amino acid modification to the amino acid sequence of SEQ ID NO:2, at an amino acid residue position number: 16, 19, 24, 25, 27, 28, 48, 101, 105, 107, 119, 141, 143, 145, 146, 147, 153, 172, 175, 179, 197, 201, 203, 205, 206, 215, 219, 220, 221, 230, 364, 366, 369, 398, 399, 438, 440, 446, 452, 453, 456, 458, 463, 464, 465, 468, 476, 490, 499, 504, 508, or any combination thereof to the amino acid sequence of SEQ ID NO:2, and the variant polypeptide has beta-amylase activity; (b) variant polypeptide is an amino acid sequence that is at least 99.4% identical to the amino acid sequence as set forth in SEQ ID NO:3, wherein the variant polypeptide has at least one single amino acid modification to the amino acid sequence of SEQ ID NO:3, at an amino acid residue position number: 16, 19, 24, 25, 27, 28, 48, 83, 101, 105, 107, 119, 141, 143, 145, 146, 147, 153 155, 172, 175, 179, 197, 201, 203,205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:3, and the variant polypeptide has beta-amylase activity; (c) variant polypeptide is an amino acid sequence that is at least 95% identical to the amino acid sequence as set forth in SEQ ID NO:4, wherein the variant polypeptide has at least one single amino acid modification to the amino acid sequence of SEQ ID NO:4, at an amino acid residue position number: 16, 19, 24, 25, 27, 28, 48, 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:4, and the variant polypeptide has beta-amylase activity; (d) the variant polypeptide is an amino acid sequence that is at least 95% identical to the amino acid sequence as set forth in SEQ ID NO:5, wherein the variant polypeptide has at least one single amino acid modification to the amino acid sequence of SEQ ID NO:5, at an amino acid residue position number: 16, 19, 24, 25, 27, 28, 48 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:5, and the variant polypeptide has beta-amylase activity; (e) the variant polypeptide is an amino acid sequence that is at least 95% identical to the amino acid sequence as set forth in SEQ ID NO:6, wherein the variant polypeptide has at least one single amino acid modification to the amino acid sequence of SEQ ID NO:6, at an amino acid residue position number: 16, 19, 24, 25, 27, 28, 48, 83, 101, 105, 107, 119, 141, 143, 145, 146, 147, 153, 155, 172, 175, 179, 197, 201, 203, 205, 206, 215, 219, 220, 221, 230, 273, 280, 286, 319, 322, 364, 366 369, 398, 399, 438, 440, 446, 452, 453, 456, 458, 463, 464, 465, 468, 476, 490, 499, 504, 508, or any combination thereof to the amino acid sequence of SEQ ID NO:6, and the variant polypeptide has beta-amylase activity; and, (f) the variant polypeptide is an amino acid sequence that is at least 95% identical to the amino acid sequence as set forth in SEQ ID NO:7, wherein the variant polypeptide has at least one single amino acid modification to the amino acid sequence of SEQ ID NO:7, at an amino acid residue position number 48, 51, 56, 57, 59, 60, 80, 115, 133, 137, 139, 151, 173, 175, 177, 178, 179, 185, 187, 204, 207, 211, 229, 233,235, 237, 238, 247, 251, 252, 253, 262, 305, 231, 318, 351, 354, 396, 398, 401, 430, 431, 470, 472, 478, 484, 485, 488, 490, 495, 496, 497, 500, 508, 522, 531, 536, 540, or any combination thereof to the amino acid sequence of SEQ ID NO:7, and the variant polypeptide has beta-amylase activity.

2. The variant polypeptide of claim 1, wherein the at least one single amino acid modification is an amino acid substitution, insertion, deletion, or any combination thereof and the variant polypeptide has beta-amylase activity.

3. The variant polypeptide of claim 2, wherein the amino acid substitution is a conservative amino acid substitution.

4. The variant polypeptide of claim 2, wherein the at least one single amino acid modification is an amino acid substitution comprising: K16Q, D19I, D19L, K24D, K24E, D25P, L27Q, L27H, L27C, I28A, K48Q, E48D, D51I, D51L, K56D, K56E, D57P, D57K, L59Q, L59H, L59C, I60A, E80D, C83S, S83C, T101N, Q105L, N107S, C115S, Si15C, N119D, T133N, Q137L, N139S, A41R, N143D, S145N, S146P, Y147H, N151D, K153E, Y155H, H155Y, S172T, A173R, N175D, W175R, S177N, S178P, G179D, Y179H, K185E, Y187H, H187Y, A197T, K201E, G203I, S204T, I205M, A206H, W207R, G211D, S215D, F219W, S220W, S220C, C220S, C220L, C220W, Q221M, A229T, N230K, K233E, G235I, I237M, A238H, S247D, F251W, S252L, S252W, S252C, C252S, C252L, C252W, Q253M, N262K, N262G, V273*, A280S, S280A, H286Y, Y286H, V305*, A312S, S312A, Y318H, H318Y, T319S, S319T, C322S, S322C, T351S, S351T, C354S, S354C, A364P, S366H, N369P, A396P, S398H, S398P, D399M, N401P, S430P, D431M, N438Y, N738S, Y440N, S446P, N452D, T453K, A456S, G458D, P463T, P463L, N464D, Y465N, W468C, N470Y, N470S, Y472N, P476L, S478P, N484D, T485K, A488S, G490D, S490T, P495T, P495L, N496D, Y497N, S499P, W500C, T504N, P508L, S508T, S522T, S531P, T536N, S540T, or any combination thereof and the variant polypeptide has beta-amylase activity.

5. A variant polypeptide having beta-amylase activity, wherein the variant polypeptide is selected from the group consisting of:
(i) the variant polypeptide is an amino acid sequence that is at least 95% identical to the amino acid sequence as set forth in SEQ ID NO:2, wherein the variant polypeptide has a combination of amino acid modifications to the amino acid sequence of SEQ ID NO:2, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, S398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f1) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (ii) the variant polypeptide is an amino acid sequence that is at least 99.4% identical to the amino acid sequence as set forth in SEQ ID NO:3, wherein the variant polypeptide has a combination of amino acid modifications to the amino acid sequence of SEQ ID NO:3, and the combination is selected from the group consisting of: (a1) D19I, L27C, A141R, A364P, N369P, S398P; (b1) D19I, L27C, I28A, S145N, G203I, S220L, A364P, N369P, S398P; (e1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, S220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A41R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A41R, A364P, N369P, S398P; (s1) K24E, D25P, L27H, A141R, G203I, S220L, S398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f1) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, S146P, K201E; (o2) D25K, L27C, S220L, A364P, N369P, S398P, N107S, S172T, W175R; (p2) D25K, L27C, S220L, A364P, N369P, S398P, Q105L, N119D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (iv) the variant polypeptide is an amino acid sequence that is at least 95% identical to the amino acid sequence as set forth in SEQ ID NO:5, wherein the variant polypeptide has a combination of amino acid modifications to the amino acid sequence of SEQ ID NO:5, and the combination is selected from the group consisting of: (a1) D19I, L27C, A141R, A364P, N369P, S398P; (b1) D19I, L27C, I28A, S145N, G203I, C220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, S398P; (g1) D25K, I28A, C220L, Q221M, A364P, N369P; (h1) D25K, L27C, G203I, A364P, N369P, S398P; (i1) D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, C220L, A364P, N369P, S398P; (n1) D25K, L27C, C220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, C220L, S398P; (t1) K24E, L27H, I28A, C220L, A364P, N369P, S398P; (u1) N143D, A197T; (v1) C220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f1) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, C220L, A364P, N369P, S398P, K153E, K201E; (n2) D25K, L27C, C220L, A364P, N369P, S398P, E48D, N143Y, S146P, K201E; (o2) D25K, L27C, C220L, A364P, N369P, S398P, N107S, S172T, W175R; (p2) D25K, L27C, C220L, A364P, N369P, S398P, Q105L, N119D; (q2) D25K, L27C, C220L, A364P, N369P, S398P, P463T; (r2) D25K, L27C, C220L, A364P, N369P, S398P, N438Y, N464D, P476L; (s2) D25K, L27C, C220L, A364P, N369P, S398P, P463L, Y465N, W468C; (t2) D25K, L27C, K153E, K201E, C220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (vi) the variant polypeptide is an amino acid sequence that is at least 95% identical to the amino acid sequence as set forth in SEQ ID NO:6, wherein the variant polypeptide has a combination of amino acid modifications to the amino acid sequence of SEQ ID NO:6, and the combination is selected from the group consisting of: (a1) D19I, L27C, A141R, A364P, N369P, S398P; (b1) D19I, L27C, I28A, S145N, G203I, S220L, A364P, N369P, S398P; (c1) D19I, L27H, Q221M; (d1) D25K, A364P, N369P, S398P; (e1) D25K, A364P, N369P, S398P; (f1) D25K, G203I, A364P, N369P, 5398P; (g1) D25K, I28A, S220L, Q221M, A364P, N369P; (h1) D25K, L27C, G203I, A364P, N369P, S398P; D25K, L27C, G203I, A364P, N369P, S398P; (j1) D25K, L27C, G203I, Q221M, A364P, N369P, S398P; (k1) D25K, L27C, I28A, A141R, A364P, N369P, S398P; (l1) D25K, L27C, I28A, A141R, A364P, N369P, S398P; (m1) D25K, L27C, S145N, S220L, A364P, N369P, S398P; (n1) D25K, L27C, S220L, A364P, N369P, S398P; (o1) D25P, L27H, I28A, Q221M; (p1) G203I, A364P, N369P, S398P; (q1) K24E, D25K, L27C, A364P, N369P; (r1) K24E, D25K, L27C, I28A, A141R, A364P, N369P, S398P; (s1) K24E, D25P, L27H, A141R, G203I, S220L, S398P; (t1) K24E, L27H, I28A, S220L, A364P, N369P, S398P; (u1) N143D, A197T; (v1) S220L, A364P, N369P, S398P; (w1) T101N, D399M; (X1) D25K, A364P, N369P, S398P, P463T; (y1) D25K, A364P, N369P, S398P, N438Y, N464D, P476L; (z1) D25K, A364P, N369P, S398P, P463L, Y465N, W468C; (a2) D25K, A364P, N369P, S398P, A456S; (b2) D25K, A364P, N369P, S398P, N438Y, Y440N; (c2) D25K, A364P, N369P, S398P, G458D; (d2) D25K, A364P, N369P, S398P, S508T; (e2) D25K, A364P, N369P, S398P, T504N; (f1) D25K, A364P, N369P, S398P, S490T; (g2) D25K, A364P, N369P, S398P, S499P; (h2) D25K, A364P, N369P, S398P, N452D; (i2) D25K, A364P, N369P, S398P, N438S; (j2) D25K, A364P, N369P, S398P, T453K; (k2) D25K, A364P, N369P, S398P, S446P; (l2) D25K, A364P, N369P, S398P, W468C; (m2) D25K, L27C, S220L, A364P, N369P, S398P, K153E, K201E; (n2) D25K, L27C, S220L, A364P, N369P, S398P, E48D, N143Y, Si46P, K201E; (o2) D25K, L27C, S220L, A364P, N369P, S398P, N107S, S172T, W175R; (p2) D25K, L27C, S220L, A364P, N369P, S398P, Q105L, Ni 19D; (q2) D25K, L27C, S220L, A364P, N369P, S398P, P463T; (r2) D25K, L27C, S220L, A364P, N369P, S398P, N438Y, N464D, P476L; (s2) D25K, L27C, S220L, A364P, N369P, S398P, P463L, Y465N, W468C; (t2) D25K, L27C, K153E, K201E, S220L, A364P, N369P, S398P, N438Y, N464D, P476L; (u2) D25K, L27C, G203I, Q221M, A364P, N369P, S398P, P463T; (v2) D25K, L27C, G203I, Q221M, A364P, N369P, S398P, N438Y, N464D, P476L; and (w2) D25K, L27C, G203I, Q221M, A364P, N369P, S398P, S398P, P463L, Y465N, W468C; wherein the variant polypeptide has beta-amylase activity; (vii) the variant polypeptide is an amino acid sequence that is at least 95% identical to the amino acid sequence as set forth in SEQ ID NO:7, wherein the variant polypeptide has a combination of amino acid modifications to the amino acid sequence of SEQ ID NO:7, and the combination is selected from the group consisting of: (a1) D51I, L59C, A173R, A396P, N401P, S430P; (b1) D51I, L59C, I60A, S177N, G235I, S252L, A3% P, N401P, S430P; (c1) D51I, L59H, Q253M; (d1) D57K, A3% P, N401P, S430P; (e1) D57K, A3% P, N401P, S430P; (f1) D57K, G235I, A396P, N401P, S430P; (g1) D57K, I60A, S252L, Q253M, A3% P, N401P; (h1) D57K, L59C, G235I, A3% P, N401P, S430P; (i1) D57K, L59C, G235I, A396P, N401P, S430P; (j1) D57K, L59C, G235I, Q253M, A396P, N401P, S430P; (k1) D57K, L59C, I60A, A173R, A3% P, N401P, S430P; (l1) D57K, L59C, I60A, A173R, A3% P, N401P, S430P; (m1) D57K, L59C, S177N, S252L, A3% P, N401P, S430P; (n1) D57K, L59C, S252L, A3% P, N401P, S430P; (o1) D57P, L59H, I60A, Q253M; (p1) G235I, A396P, N401P, S430P; (q1) K56E, D57K, L59C, A3% P, N369P; (r1) K56E, D57K, L59C, I60A, A173R, A3% P, N401P, S430P; (s1) K56E, D57P, L59H, A173R, G235I, S252L, S430P; (t) K56E, L59H, I60A, S252L, A3% P, N401P, S430P; (u1) N175D, A229T; (v1) S252L, A3% P, N401P, S430P; (w1) T133N, D431M; (x1) D57K, A3% P, N401P, S430P, P495T; (y1) D57K, A3% P, N401P, S430P, N470Y, N496D, P508L; (z1) D57K, A396P, N401P, S430P, P495L, Y497N, W500C; (a2) D57K, A3% P, N401P, S430P, A488S; (b2) D57K, A3% P, N401P, S430P, N470Y, Y472N; (c2) D57K, A3% P, N401P, S430P, G490D; (d2) D57K, A3% P, N401P, S430P, S540T; (e2) D57K, A3% P, N401P, S430P, T540N; (f1) D57K, A396P, N401P, S430P, S522T; (g2) D57K, A3% P, N401P, S430P, S531P; (h2) D57K, A3% P, N401P, S430P, N484D; (i2) D57K, A3% P, N401P, S430P, N470S; (j2) D57K, A3% P, N401P, S430P, T485K; (k2) D57K, A3% P, N401P, S430P, S478P; (l2) D57K, A3% P, N401P, S430P, W500C; (m2) D57K, L59C, S252L, A396P, N401P, S430P, K185E, K233E; (n2) D57K, L59C, S252L, A3% P, N401P, S430P, E48D, N175Y, S178P, K233E; (o2) D57K, L59C, S252L, A3% P, N401P, S430P, N139S, S204T, W207R; (p2) D57K, L59C, S252L, A3% P, N401P, S430P, Q137L, N151D; (q2) D57K, L59C, S252L, A3% P, N401P, S430P, P495T; (r2) D57K, L59C, S252L, A3% P, N401P, S430P, N470Y, N4% D, P508L; (s2) D57K, L59C, S252L, A3% P, N401P, S430P, P495L, Y497N, W500C; (t2) D57K, L59C, K185E, K233E, S252L, A3% P, N401P, S430P, N470Y, N496D, P508L; (u2) D57K, L59C, G235I, Q253M, A396P, N401P, S430P, P495T; (v2) D57K, L59C, G235I, Q253M, A3% P, N401P, S430P, N470Y, N4% D, P508L; (w2) D57K, L59C, G235I, Q253M, A396P, N401P, S430P, P495L, Y497N, W500C; wherein the variant polypeptide has beta-amylase activity.

6. A variant polypeptide having beta-amylase activity, wherein the variant polypeptide is an amino acid sequence that is at least 95% identical to the amino acid sequence as set forth in SEQ ID NO:2, and the variant polypeptide has an increase in enzyme activity, thermostability, pH-stability, or any combination thereof when compared to the beta-amylase of SEQ ID NO:2.

7. The variant polypeptide of claim 1, wherein the variant polypeptide is a fragment of the full length amino acid sequence and the fragment has beta-amylase activity.

\* \* \* \* \*